US012209949B2

(12) United States Patent
Caldwell et al.

(10) Patent No.: US 12,209,949 B2
(45) Date of Patent: Jan. 28, 2025

(54) FILTERLESS NON-DISPERSIVE INFRARED SENSING DEVICES AND METHODS

(71) Applicants: Vanderbilt University, Nashville, TN (US); Third Floor Materials, Inc., Durham, NC (US)

(72) Inventors: Joshua D. Caldwell, Nashville, TN (US); Edward Sachet, Nashville, TN (US); Christopher Shelton, Nashville, TN (US); Thomas G. Folland, Nashville, TN (US)

(73) Assignees: Vanderbilt University, Nashville, TN (US); Third Floor Materials, Inc., Durham, NC (US)

( * ) Notice: Subject to any disclaimer, the term of this patent is extended or adjusted under 35 U.S.C. 154(b) by 160 days.

(21) Appl. No.: 18/096,319

(22) Filed: Jan. 12, 2023

(65) Prior Publication Data

US 2023/0221242 A1 Jul. 13, 2023

Related U.S. Application Data

(60) Provisional application No. 63/298,915, filed on Jan. 12, 2022.

(51) Int. Cl.
*G01N 21/17* (2006.01)
*G01N 33/00* (2006.01)

(52) U.S. Cl.
CPC ..... *G01N 21/1702* (2013.01); *G01N 33/0027* (2013.01); *G01N 2021/1704* (2013.01); *G01N 2201/061* (2013.01)

(58) Field of Classification Search
CPC .......... G01N 21/1702; G01N 33/0027; G01N 2021/1704; G01N 2201/061; G01N 21/3504; G01N 33/004
See application file for complete search history.

(56) References Cited

U.S. PATENT DOCUMENTS

2020/0386718 A1\* 12/2020 Singh ................. G01N 21/4795
2022/0107263 A1\* 4/2022 Biesinger .............. G01J 3/0232

OTHER PUBLICATIONS

A. Lochbaum, A. Dorodnyy, U. Koch, S. M. Koepfli, S. Volk, Y. Fedoryshyn, V. Wood, and J. Leuthold, Nano Lett. 20, 4169 (2020).
J. Hodgkinson and R. P. Tatam, 24, 43 (2013).
F. H. L. Koppens, T. Mueller, P. Avouris, A. C. Ferrari, M. S. Vitiello, and M. Polini, Nat. Nanotechnol. 9, 780 (2014).
(Continued)

*Primary Examiner* — Suman K Nath
(74) *Attorney, Agent, or Firm* — Meunier Carlin & Curfman LLC

(57) ABSTRACT

Devices and methods for non-dispersive infrared (NDIR) sensing are disclosed. In one aspect, a non-dispersive infrared sensor is disclosed which, in one embodiment includes a nanophotonic infrared emitting metamaterial (NIREM) emitter configured to selectively emit radiation corresponding to a respective vibrational resonance frequency for each of a plurality of different analytes of interest. The broadband detector can be configured to detect photons associated with vibrational resonance of each of the plurality of analytes of interest in response to the emitted radiation from the NIREM emitter, in order to determine properties of one or more of the analytes of interest.

20 Claims, 28 Drawing Sheets

(56) References Cited

OTHER PUBLICATIONS

T. G. Folland, L. Nordin, D. Wasserman, and J. D. Caldwell, J. Appl. Phys. 125, (2019).
M. De Zoysa, T. Asano, K. Mochizuki, A. Oskooi, T. Inoue, and S. Noda, Nat. Photonics 6, 535 (2012).
T. Inoue, M. De Zoysa, T. Asano, and S. Noda, 24, 899 (2016).
J. J. Greffet, R. Carminati, K. Joulain, J. P. Mulet, S. Mainguy, and Y. Chen, Nature 416, 61 (2002).
G. Lu, R. J. Nolen, T. G. Folland, M. Tadjer, D. G. Walker, and J. D. Caldwell, ACS Omega (n.d.).
T. Wang, P. Li, D. N. Chigrin, A. J. Giles, F. J. Bezares, O. J. Glembocki, J. D. Caldwell, and T. Taubner, ACS Photonics 4, 1753 (2017).
J. A. Schuller, T. Taubner, and M. L. Brongersma, Nat. Photonics 3, 658 (2009).
A. Howes, J. R. Nolen, J. D. Caldwell, and J. Valentine, Adv. Opt. Mater. 8, 1 (2020).
J. A. Mason, S. Smith, and D. Wasserman, 241105, 15 (2011).
D. G. Baranov, Y. Xiao, I. A. Nechepurenko, A. Krasnok, A. Alù, and M. A. Kats, Nat. Mater. 18, 920 (2019).
J. D. Caldwell, O. J. Glembocki, Y. Francescato, N. Sharac, V. Giannini, F. J. Bezares, J. P. Long, J. C. Owrutsky, I. Vurgaftman, J. G. Tischler, V. D. Wheeler, N. D. Bassim, L. M. Shirey, R. Kasica, and S. A. Maier, Nano Lett. 13, 3690 (2013).
X. Liu, T. Tyler, T. Starr, A. F. Starr, N. M. Jokerst, and W. J. Padilla, Phys. Rev. Lett. 107, 4 (2011).
N. I. Landy, S. Sajuyigbea, J. J. Mock, D. R. Smith, and W. J. Padilla, (2008).
A. Lochbaum, Y. Fedoryshyn, A. Dorodnyy, U. Koch, C. Hafner, and J. Leuthold, ACS Photonics 4, 1371 (2017).
S. Vassant, J.-P. Hugonin, F. Marquier, and J.-J. Greffet, Opt. Express 20, 23971 (2012).
S. Campione, I. Brener, and F. Marquier, Phys. Rev. B 91, 121408 (2015).
K. P. Kelley, E. Sachet, C. T. Shelton, and J. P. Maria, APL Mater. 5, 0 (2017).
E. L. Runnerstrom, K. P. Kelley, E. Sachet, C. T. Shelton, and J. P. Maria, ACS Photonics (2017).
J. R. Nolen, E. L. Runnerstrom, K. P. Kelley, T. S. Luk, T. G. Folland, A. Cleri, J.-P. Maria, and J. D. Caldwell, Phys. Rev. Mater. 4, 1 (2020).
K. P. Kelley, E. L. Runnerstrom, E. Sachet, C. T. Shelton, E. D. Grimley, A. Klump, J. M. Lebeau, Z. Sitar, J. Y. Suen, W. J. Padilla, and J.-P. Maria, ACS Photonics 6, 1139 (2019).
E. Sachet, C. T. Shelton, J. S. Harris, B. E. Gaddy, D. L. Irving, S. Curtarolo, B. F. Donovan, P. E. Hopkins, P. A. Sharma, A. L. Sharma, J. Ihlefeld, S. Franzen, and J. P. Maria, Nat. Mater. 14, 414 (2015).
M. Malerba, A. Alabastri, E. Miele, P. Zilio, M. Patrini, D. Bajoni, G. C. Messina, M. Dipalo, A. Toma, R. P. Zaccaria, and F. De Angelis, Nat. Sci. Reports 5, (2015).
A. G. Nikitin, A. V Kabashin, and H. Dallaporta, 20, 27941 (2012).
V. G. Kravets, F. Schedin, and A. N. Grigorenko, 087403, 1 (2008).
V. Giannini, Y. Francescato, H. Amrania, C. C. Phillips, and S. A. Maier, Nano Lett. 11, 2835 (2011).
B. S. Simpkins, J. P. Long, O. J. Glembocki, J. Guo, and J. D. Caldwell, 20, 18178 (2012).
R. Adato, A. A. Yanik, J. J. Amsden, D. L. Kaplan, F. G. Omenetto, M. K. Hong, S. Erramilli, and H. Altug, Proc. Natl. Acad. Sci. 106, 19227 (2009).
R. Adato, A. Artar, S. Erramilli, and H. Altug, (2013).
E. L. Runnerstrom, K. P. Kelley, E. Sachet, C. T. Shelton, and J. P. Maria, ACS Photonics 4, 1885 (2017).
N. C. Passler and A. Paarmann, J. Opt. Soc. Am. B 34, 2128 (2017).

\* cited by examiner

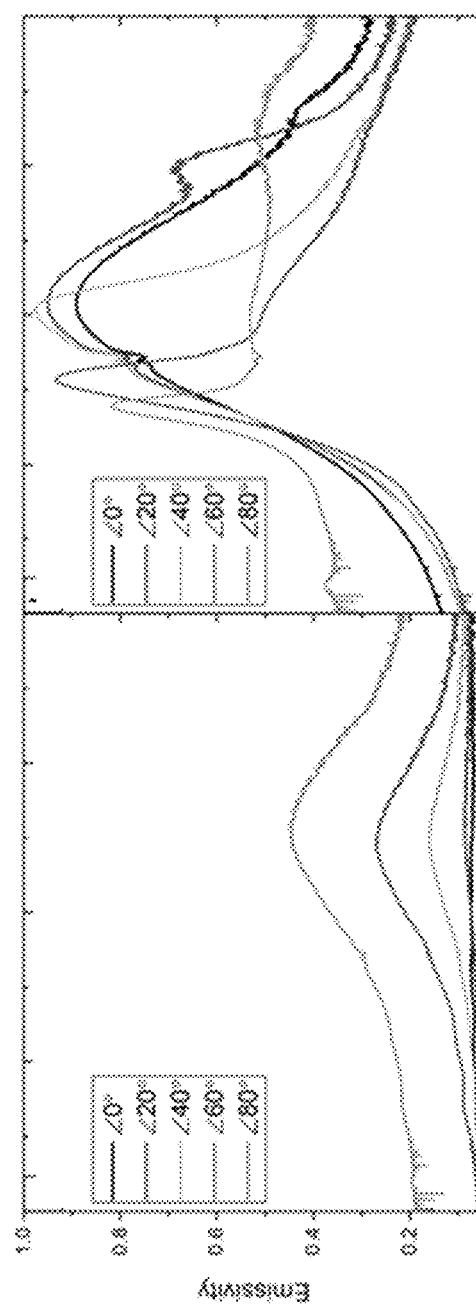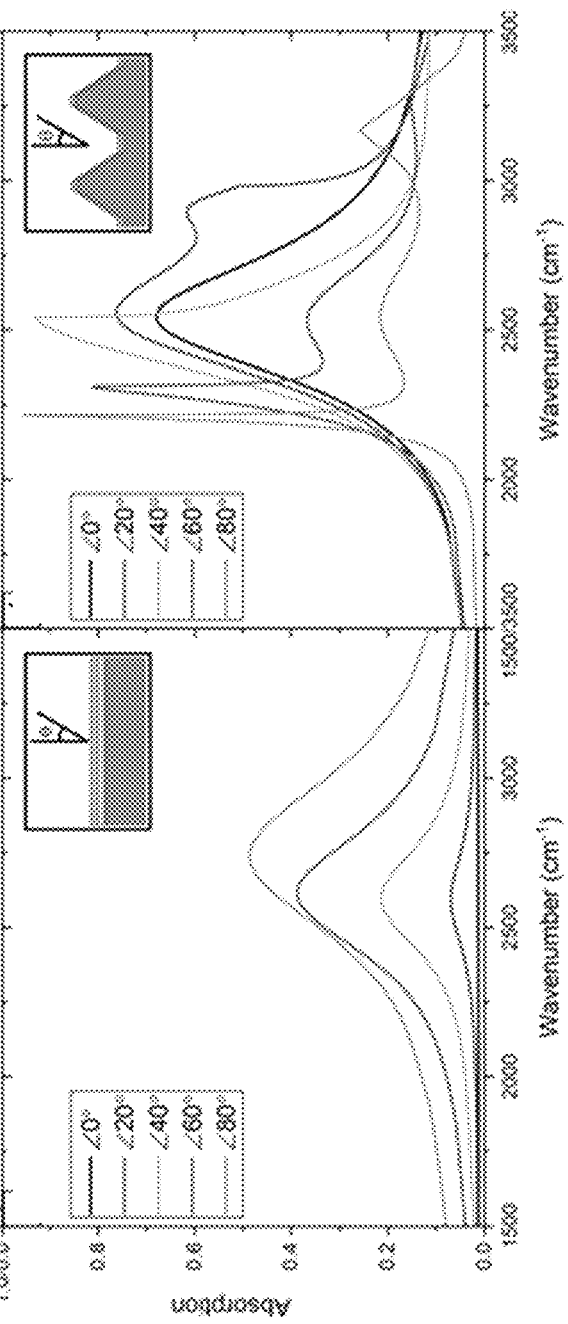
FIG. 2A  FIG. 2B  FIG. 2C  FIG. 2D

1400

1402

Selectively emitting, by a nanophotonic infrared emitting metamaterial (NIREM) emitter, radiation corresponding to a respective vibrational resonance frequency of each of a plurality of different analytes of interest

1404

Detecting, by a broadband detector, photons associated with vibrational activity of the analytes of interest in response to the emitted radiation

FIG. 14

FILTERLESS NON-DISPERSIVE INFRARED SENSING DEVICES AND METHODS

CROSS-REFERENCE TO RELATED APPLICATION

This application claims priority to, and the benefit of, Provisional Patent Application No. 63/298,915 filed Jan. 12, 2022, the entire contents of which is hereby incorporated by reference.

STATEMENT REGARDING GOVERNMENT SUPPORT

This invention was made with government support under grant number N00014-18-1-2107 awarded by the Office of Naval Research, grant number 1560414 awarded by the National Science Foundation, and grant number H9240519P0015 awarded by the United States Special Operations Command (USSOCOM) Small Business Innovation Research (SBIR). The government has certain rights in the invention.

BACKGROUND

Molecular sensing plays a critical role in a variety of applications such as chemical and industrial manufacturing, oil and gas exploration and extraction, defense and security as well as environmental safety. For many industrial and manufacturing applications detecting and identifying low concentrations of harmful gases and byproducts are performed using non-dispersive infrared (NDIR) sensors. These devices utilize a broadband IR emitter, thermopile detector and a spectrally narrow bandpass filter tuned to a vibrational resonance of the analyte of interest. However, such filters can be expensive to fabricate and limit the NDIR to operation at only a single frequency, unless filter wheels are employed, which can expand the size and complexity of the device.

Many schemes exist for the detection of chemical species, for gases with characteristic absorption bands within the infrared, infrared spectroscopy is commonly used and has advantages over other techniques. [1]. This can be achieved through exploitation of the Beer-Lambert law demonstrating that a reduction in the transmission of IR light resonant with a molecular vibrational absorption over a defined cross-sectional area and path length is directly proportional to the concentration of that molecule in the gas cell. This implies that for infrared detection there is a need for either a spectroscopic solution, such as Fourier transform infrared (FTIR) spectroscopy, or a single frequency excitation/detection scheme. In the case of the latter, a number of potential solutions arise: 1) implementation of a broadband light source and detector pair, with a narrow bandpass filter, 2) implementation of a narrow band detector with a broadband source [2], or 3) use a narrow band source with a broadband detector. A platform supporting both a narrow band source and detector pair, such as the MEMS-based sensor designed by Lochbaum et. al. [3], is another potential solution. Here, while the signal-to-noise ratio is enhanced resulting in similar sensitivity and selectivity performance to conventional methods in a significantly smaller device, the single, narrow bandwidth resonance supported by the metamaterial perfect absorber-based emitter and detector precludes multifrequency operation.

The first solution is the basis for non-dispersive infrared (NDIR) gas sensors that are widely implemented in industry due to their device simplicity. [4]. However, these come with the inherent limitation of only operating at a single fixed frequency band, and the inclusion of sufficiently narrow bandpass filters results in significant increases in cost. Multiple frequencies can be measured via NDIR through the incorporation of a filter wheel featuring multiple bandpass filters, however, this significantly increases the cost, size and complexity of the device. Thus, some implementations of an NDIR approach would implement a simple narrowband source or detector to eliminate these challenges, while still maintaining the standard form factor and sensitivity of commercial NDIR systems.

One way to eliminate the need for a narrow bandpass filter within NDIR designs is to integrate a similarly narrow bandwidth detector. Such systems have been demonstrated using a broad range of materials, for instance graphene resonator designs and plasmonic resonant structures. [2,5] However, these can require extensive nanoscale lithographic fabrication, resulting in increases in cost and complexity, while in many cases also limiting the absorptivity of the device. A similar approach is to integrate Bragg mirrors in order to resonantly enhance detection, but this requires the accurate growth of thick mirror layers. [2]. Alternatively, a narrow band source can be used, for example by incorporating an IR laser, however, within the molecular fingerprint window (500-3500 $cm^{-1}$) this can require quantum cascade lasers (QCLs) or gas lasers [6], both of which can have large electrical power and cost requirements. Although it is possible to make very sensitive gas sensors using these schemes, such approaches may be undesirable for some industrial settings where low cost and compact solutions are desired. Mid-infrared LEDs have become increasingly more appealing for such applications, however, these devices still have low output power and relatively broadband emission, which results in a high probability of cross-talk with other absorbing gases, that is, other molecular species have vibrational resonances that fall within the linewidth of the emitter. Thus, a reduction in transmission may in fact be due to the presence of another molecule than the target, eliminating the specificity of the measurement.

Recently, photonic crystals [7-9], polaritonic [10-13] and metamaterial [14,15] designs have been employed to control thermal emissivity and realize narrow-band IR sources. [16]. These nanophotonic infrared emitting metamaterials (NI-REMs) have been designed to exhibit linewidths approaching that of the molecular vibrations themselves [12,17], illustrating the potential for targeted and sensitive measurements. Such metamaterials implementing the so-called perfect absorber geometry [18,19] have been demonstrated for an advanced NDIR approach, illustrating similar sensitivity to $CO_2$ as commercial devices, without the requirement of a bandpass filter. [20]. Yet, electron beam lithography [20] was required to fabricate the metallic nanostructures necessary to stimulate the localized surface plasmon polariton (SPP) resonances within the mid-IR, the spectral range for which the device was designed. Among other challenges that remain, there is a need for dictating the radiation pattern (spatial coherence and directionality) so that the light is directed preferentially towards the detector, in eliminating strong angular dispersion of the emitted frequency, and realizing unity emissivity of both p- and s-polarized light.

SUMMARY

In some aspects, the present disclosure relates to devices and methods for non-dispersive infrared sensing.

In one aspect, the present disclosure relates to a non-dispersive infrared (NDIR) sensor, which in one embodiment includes a nanophotonic infrared emitting metamaterial (NIREM) emitter and a broadband detector. The NIREM emitter is configured to selectively emit radiation corresponding to a respective vibrational resonance frequency for each of a plurality of different analytes of interest. The broadband detector is configured to detect photons from the NIREM emitter, including photons associated with interactions of the emitted radiation from the NIREM emitter with an analyte of interest and corresponding to the respective vibrational resonance frequency, such as to determine one or more properties of the analyte of interest.

In one embodiment, the one or more properties include the concentration of at least one of the analytes of interest.

In one embodiment, the NIREM emitter includes a plurality of different emitters, each configured to emit radiation corresponding to a vibrational resonance frequency of a different analyte of interest.

In one embodiment, each of the plurality of different emitters is selectively and individually activatable for emission.

In one embodiment, the NIREM emitter is configured such that: a first emitter of the plurality of different emitters is activatable at a first time to emit radiation corresponding to a vibrational resonance frequency of a first analyte of interest; and a second emitter of the plurality of different emitters is activatable at a second time to emit radiation corresponding to a vibrational resonance frequency of a second analyte of interest, wherein the first time is different from the second time and the first analyte of interest is different from the second analyte of interest.

In one embodiment, the plurality of different emitters are arranged in an array.

In one embodiment, the NIREM emitter includes a patterned sapphire substrate (PSS) combined with a CdO film supporting an ENZ/Berreman optical mode.

In one embodiment, the NIREM emitter is configured for s-polarized thermal emission and/or p-polarized thermal emission.

In one embodiment, the broadband detector includes a thermopile.

In one embodiment, the plurality of different analytes of interest includes $CO_2$.

In another aspect, the present disclosure relates to a method for non-dispersive infrared (NDIR) sensing, which in one embodiment includes selectively emitting, by a nanophotonic infrared emitting metamaterial (NIREM) emitter, radiation corresponding to a respective vibrational resonance frequency of each of a plurality of different analytes of interest. The method also includes detecting, by a broadband detector, photons associated with vibrational activity of the analytes of interest in response to the emitted radiation.

In one embodiment, the method further includes determining, based on the photon detection, one or more properties of at least one of the analytes of interest.

In one embodiment, the one or more properties include the concentration of at least one of the analytes of interest.

In one embodiment, the NIREM emitter includes a plurality of different emitters, each configured to emit radiation corresponding to a vibrational resonance frequency of one or more analytes of interest.

In one embodiment, each of the plurality of different emitters is selectively and individually activatable for emission, and wherein the step of selectively emitting radiation includes: selectively activating a first emitter of the plurality of different emitters, at a first time, to emit radiation corresponding to a vibrational resonance frequency of a first analyte of interest, and selectively activating a second emitter of the plurality of different emitters, at a second time, to emit radiation corresponding to a vibrational resonance frequency of a second analyte of interest, wherein the first time is different from the second time and the first analyte of interest is different from the second analyte of interest.

In one embodiment, the plurality of different emitters are arranged in an array.

In one embodiment, the NIREM emitter includes a patterned sapphire substrate (PSS) combined with a CdO film supporting an ENZ/Berreman optical mode.

In one embodiment, the NIREM emitter is configured for s-polarized thermal emission and/or p-polarized thermal emission.

In one embodiment, the broadband detector includes a thermopile.

In one embodiment, the plurality of different analytes of interest includes $CO_2$.

Other aspects and features according to the example embodiments of the present disclosure will become apparent to those of ordinary skill in the art, upon reviewing the following detailed description in conjunction with the accompanying figures.

BRIEF DESCRIPTION OF THE DRAWINGS

Reference will now be made to the accompanying drawings, which are not necessarily drawn to scale.

FIGS. 1A-1D illustrate schematics of NDIR sensors and film configurations, wherein:

FIG. 1A illustrates a non-dispersive infrared (NDIR) sensor with a broadband emitter; FIG. 1B illustrates an NDIR sensor design including nanophotonic infrared emitting metamaterials NIREM; FIG. 1C illustrates a 120 nm In:CdO film deposited onto a 110 nm Au-coated flat sapphire substrate; and FIG. 1D illustrates a perspective and top view of a PSS sample with labelled geometry, using the same layer thicknesses shown in FIG. 1C.

FIGS. 2A-2D illustrate thermal emission measurements, wherein: FIG. 2A illustrates angle-dependent thermal emission measurements of the flat CdO film sample shown in the inset of FIG. 2C; FIG. 2B illustrates angle-dependent thermal emission measurements of the CdO on PSS sample shown in the inset of FIG. 2D; FIG. 2C illustrates the simulated angle-dependent absorption spectra for the flat CdO sample; and FIG. 2D illustrates the simulated angle-dependent absorption spectra for the CdO on PSS sample.

FIGS. 3A-3D illustrate polar peak emissivity plots, wherein FIG. 3A illustrates CdO on PSS and FIG. 3B illustrates CdO flat film samples. The black line in FIGS. 3A and 3B represents the measured angle-dependent, unpolarized emissivity and the red line is the simulated angle-dependent, unpolarized absorption. FIG. 3C illustrates contour plots showing the measured emissivity of the CdO PSS NIREM, and FIG. 3D illustrates the measured emissivity of the CdO Berreman film.

FIG. 4A illustrates the Z-oriented electric field ($E_z$) and Poynting vector ($\vec{P}$) of ENZ mode (2550 cm$^{-1}$) and FIG. 4B illustrates the Z-oriented $E_z$ and $\vec{P}$ of diffractive mode (3000 cm$^{-1}$).

FIGS. 7A-7F illustrate thermal emission spectra and corresponding film geometries, wherein: FIG. 7A illustrates s-polarized thermal emission from the film geometry shown in FIG. 7E; FIG. 7B illustrates the s-polarized thermal emission from the film geometry shown in FIG. 7F; FIG. 7C illustrates the p-polarized thermal emission from the film geometry shown in FIG. 7E; FIG. 7D illustrates the p-polarized thermal emission spectra for the film geometry shown in FIG. 7F; FIG. 7E illustrates a CdO flat film sample; and FIG. 7F illustrates a CdO on PSS sample.

FIGS. 8A-8D illustrate contour plots, film geometry (including the pitch "p") and spectral dispersion, wherein: FIG. 8A illustrates the simulated angle-dependent p-polarized absorption for p=2.8 µm; FIG. 8B illustrates the simulated angle-dependent p-polarized absorption for p=3.02 µm; FIG. 8C illustrates the simulated angle-dependent p-polarized absorption for p=3.2 µm; FIG. 8D illustrates a top view of CdO on PSS sample with the pitch labelled.

FIG. 11A-11C illustrate film geometries, wherein: FIG. 11A illustrates a cross sectional view including cone heights and thicknesses; FIG. 11B illustrates a cone geometry viewed from normal incidence; and FIG. 11C illustrates cone geometry viewed from 22° angle of incidence.

FIGS. 12A-12B illustrate an experimental setup, wherein FIG. 12A illustrates an experimental setup showing external, angle-dependent thermal emission rig and FIG. 12B illustrates a backport for angular rig as well as external backport thermal emission device used for gas cell measurements.

FIG. 14 illustrates a method for NDIR sensing, according to embodiments of the present disclosure.

DETAILED DESCRIPTION

Figure 1A:
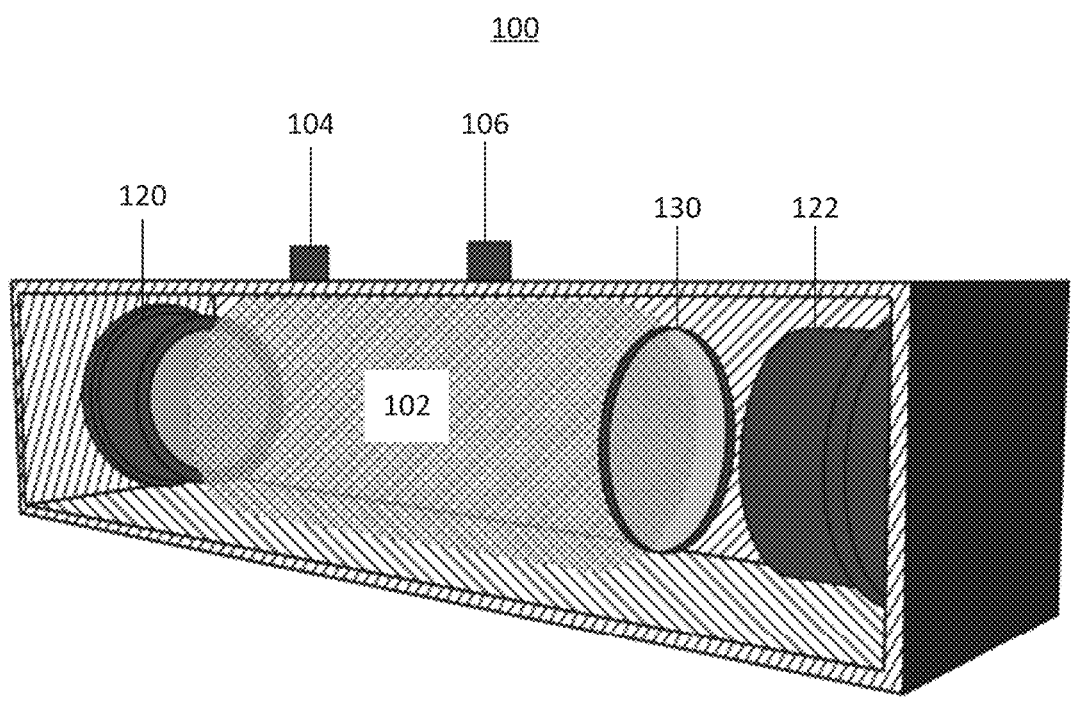

In some aspects, the present disclosure relates to non-dispersive infrared sensing devices and methods. Although example embodiments of the present disclosure are explained in detail herein, it is to be understood that other embodiments are contemplated. Accordingly, it is not intended that the present disclosure be limited in its scope to the details of construction and arrangement of components set forth in the following description or illustrated in the drawings. The present disclosure is capable of other embodiments and of being practiced or carried out in various ways.

It must also be noted that, as used in the specification and the appended claims, the singular forms "a," "an" and "the" include plural referents unless the context clearly dictates otherwise. Certain values may be expressed in terms of ranges "from" one value "to" another value. When a range is expressed in terms of "from" a particular lower value "to" a particular higher value, or "from" a particular higher value "to" a particular lower value, the range includes the particular lower value and the particular higher value.

By "comprising" or "containing" or "including" is meant that at least the named compound, element, particle, or method step is present in the composition or article or method, but does not exclude the presence of other compounds, materials, particles, method steps, even if the other such compounds, material, particles, method steps have the same function as what is named.

In describing example embodiments, terminology will be resorted to for the sake of clarity. It is intended that each term contemplates its broadest meaning as understood by those skilled in the art and includes all technical equivalents that operate in a similar manner to accomplish a similar purpose. It is also to be understood that the mention of one or more steps of a method does not preclude the presence of additional method steps or intervening method steps between those steps expressly identified. Steps of a method may be performed in a different order than those described herein without departing from the scope of the present disclosure. Similarly, it is also to be understood that the mention of one or more components in a device or system does not preclude the presence of additional components or intervening components between those components expressly identified.

Some references, which may include various patents, patent applications, and publications, are cited in a reference list and discussed in the disclosure provided herein. The citation and/or discussion of such references is provided merely to clarify the description of the present disclosure and is not an admission that any such reference is "prior art" to any aspects of the present disclosure described herein. In terms of notation, "[n]" corresponds to the $n^{th}$ reference in the list. For example, "[3]" refers to the $3^{rd}$ reference in the list, namely A. Lochbaum, A. Dorodnyy, U. Koch, S. M. Koepfli, S. Volk, Y. Fedoryshyn, V. Wood, and J. Leuthold, Nano Lett. 20, 4169 (2020). All references cited and discussed in this specification are incorporated herein by reference in their entireties and to the same extent as if each reference was individually incorporated by reference.

Some experimental data are presented herein for purposes of illustration and should not be construed as limiting the scope of the present disclosure in any way or excluding any alternative or additional embodiments.

A detailed description of aspects of the present disclosure, in accordance with various example embodiments, will now be provided with reference to the accompanying drawings. The drawings form a part hereof and show, by way of illustration, specific embodiments and examples. In referring to the drawings, like numerals represent like elements throughout the several figures.

Embodiments of the present disclosure include a nanophotonic infrared emitting metamaterial (NIREM) fabricated from thin films of doped CdO grown on patterned sapphire substrates (PSS) that exhibit narrow band thermal emission. By coupling this emitter with a simple broadband detector such as a thermopile, the functionality of the NDIR sensor can be replicated without the need for a filter. Unlike some metamaterial-based emitters, embodiments of the present disclosure can emit both p- and s-polarized light with near-unity emissivity at angles ranging from 0 to 40° off the surface normal. Described herein are implementations of NIREMs for $CO_2$ gas detection within an FTIR spectrometer, demonstrating performance comparable with a conventional black-body as a light source, however implementations of NIREMs for other gasses are contemplated by the present disclosure.

Embodiments of the present disclosure include NIREMs that can provide a suitable plug-and-play replacement for NDIR devices as they can be implemented in a form-factor commensurate or significantly reduced in comparison to the current state of the art. Additionally, embodiments of the present disclosure can incorporate multiple NIREM dies tuned to emit at different frequencies, and multiple vibrational modes can be sequentially detected, making the approach amenable to identification and quantification of complicated molecules within a single NDIR configuration. As a non-limiting example, embodiments of the present disclosure can implement devices that include the narrowband, near-unity absorption of both p- and s-polarized light (>0.95 from 0-40° off the surface normal) facilitated via epsilon-near-zero (ENZ) modes [21,22] within thin films (<150 nm) of n-type, In-doped CdO (In:CdO) grown on patterned sapphire substrates (PSS).

FIGS. 1A-1D illustrate different configurations of emitters and detectors. FIG. 1A depicts a device 100 for performing NDIR sensing on a gas 102. The gas 102 can be introduced to the device at a gas inlet 104, and exit the device through a gas outlet 106. Optionally, the gas can flow continuously between the gas inlet 104 and gas outlet 106, or the gas 102 can enter/exit the device periodically.

The device 100 shown in FIG. 1A includes an emitter/detector pair. In the example device 100, the emitter is a broadband emitter 120, and the detector is a thermopile detector 122. One or more optical filters 130 can be spaced between the broadband emitter 120 and thermopile detector 122, so that emissions from the broadband emitter 120 pass through the gas 102 and the optical filters 130 before reaching the thermopile detector 122.

In some embodiments, the broadband emitter 120 is a nanophotonic infrared emitting metamaterial (NIREM) emitter configured to selectively emit radiation corresponding to a respective vibrational resonance frequency for each of a plurality of different analytes of interest. Optionally, the NIREM emitter can include more than one emitter, where the one or more emitters can be configured to emit radiation corresponding to a vibration resonance frequency of different analytes of interest. The one or more emitters in an NIREM emitter can activatable separately and individually activatable. In some embodiments, different emitters from the NIREM emitter can be activated during different time periods so that the NIREM emitter emits radiation corresponding to vibrational resonance frequencies of different analytes of interest at different times. As a non-limiting example, at a first time, or during a first time period, a first emitter can be activated to emit radiation corresponding to the vibrational resonance frequency of a first analyte of interest. And, at a second time, or during a second time period, a second emitter can be activated to emit radiation corresponding to the vibrational resonance frequency of a second analyte of interest. The first time and second times can be different, and the first analyte of interest and second analyte of interest can also be different.

Different types of emitters are contemplated by the present disclosure. Optionally, the NIREM emitter can include a PSS. Optionally the PSS can include a CdO film supporting an ENZ/Berreman mode. Alternatively or additionally, the NIREM emitter can include emitters formed in an array. Optionally, the NIREM emitter can be configured for s-polarized thermal emission and/or p-polarized thermal emission.

The detector can be configured to detect photons from the NIREM emitter, including photons associated with interactions of the emitted radiation from the NIREM emitter with an analyte of interest in the gas 102 and corresponding to the respective vibrational resonance frequency, such as to determine one or more properties of the analyte of interest. A non-limiting example of a property of the analyte of interest can include the concentration of the analyte of interest in the gas 102. In some embodiments, the analyte of interest is $CO_2$.

Figure 1B:
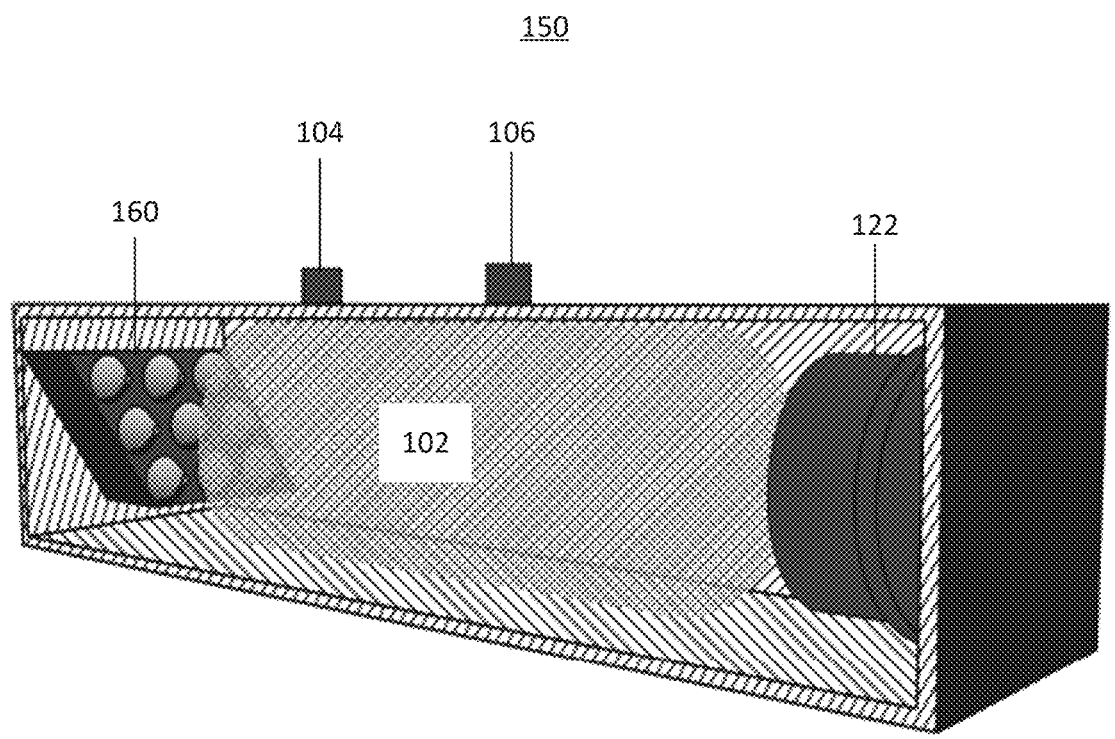

Embodiments of the present disclosure can include devices with narrowband sources (i.e., narrowband emitters). FIG. 1B illustrates a device 150 including an emitter/detector pair positioned on opposite sides of a gas inlet 104 and gas outlet 106. In the example device 150, the emitter is a narrowband emitter 160, and the detector is a thermopile detector 122. In some embodiments, the thermopile detector 122 is configured as a broadband detector. It should be understood that thermopile detector 122 shown in FIG. 1A and FIG. 1B can be replaced with a broadband detector other than a thermopile detector 122, and that the thermopile detector 122 shown in FIGS. 1A and 1B is intended only as a non-limiting example. In the embodiment shown in FIG. 1B, the narrowband emitter 160 can include a film configured to filter the wavelengths of light emitted. The filtered light passes through the gas 102, before reaching the thermopile detector 122. In the embodiment shown in FIG. 1B, the optical filters 130 shown in FIG. 1A are not required because the emitter is a narrowband emitter 160.

Figure 1C:
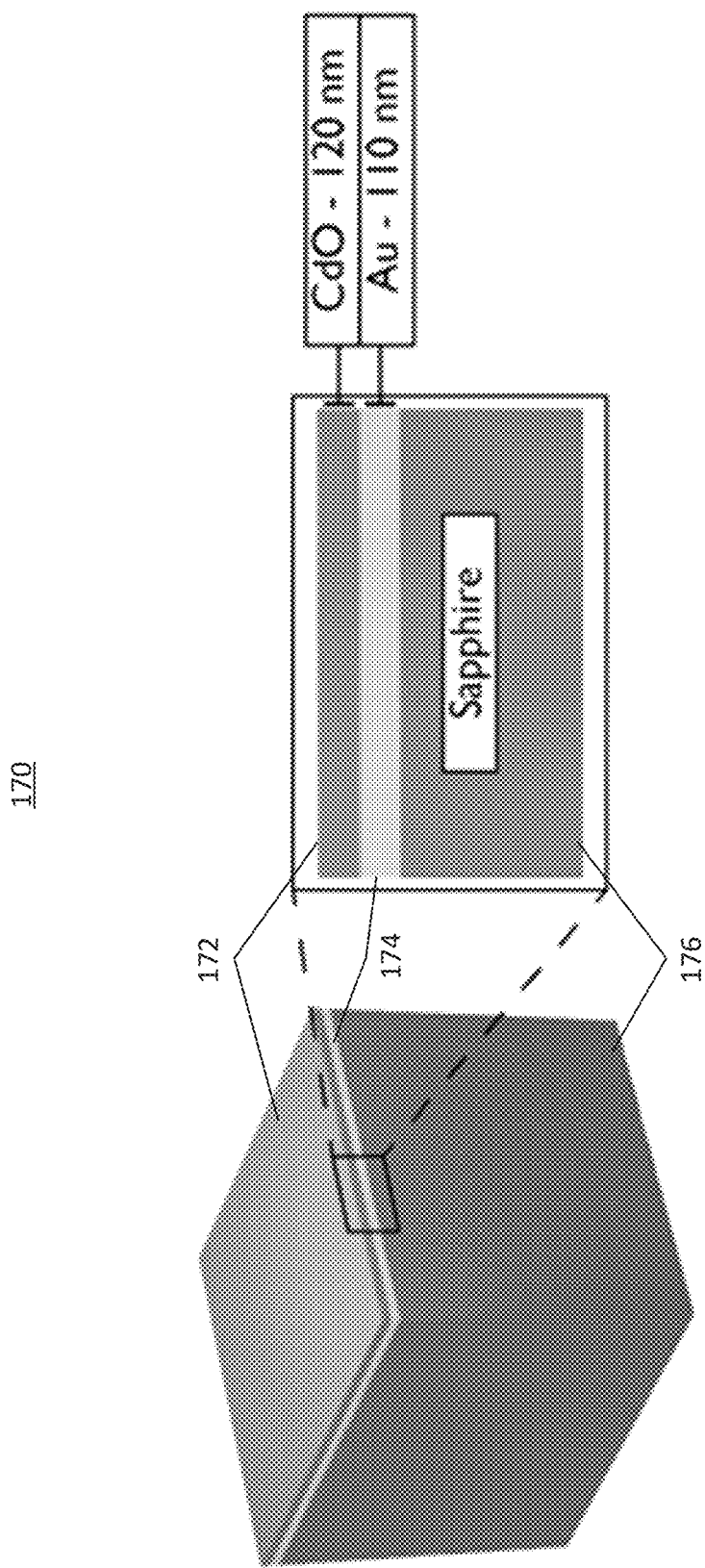

The narrowband emitter 160 can be formed by placing a film on an emitter (e.g., a broadband emitter). FIG. 1C illustrates a cross section of an example structure 170 that can be used in the narrowband emitter 160 shown in FIG. 1B. The structure 170 can include a CdO film 172 deposited on an Au layer 174, and the Au layer 174 can be formed on a PSS 176. In the example embodiment shown in FIG. 1C, the CdO film 172 is 120 nm thick, the Au layer 174 is 110 nm thick, but it should be understood that these are only non-limiting examples and that other thicknesses are contemplated by the present disclosure. Moreover, it should be understood that throughout the present disclosure the terms "layer" and "film" are used interchangeably to refer to materials deposited on a surface, for example materials deposited on a substrate.

Embodiments of the present disclosure include NIREM devices based on the strong absorption of the Berreman and ENZ modes within thin films of polaritonic media. The Berreman mode, along with the ENZ polariton mode that is its sub-diffractional counterpart, are the result of strong coupling between surface polaritons supported on the opposing interfaces of a thin film. [21]. Thin films of In:CdO on the order of 120 nm thick illustrated in FIG. 1C support both Berreman and ENZ modes, with the former being accessible from free-space and providing near-unity absorption of p-polarized light at angles near the Brewster angle. [26] The use of different film materials and film thicknesses is contemplated by the present disclosure.

Figure 1D:
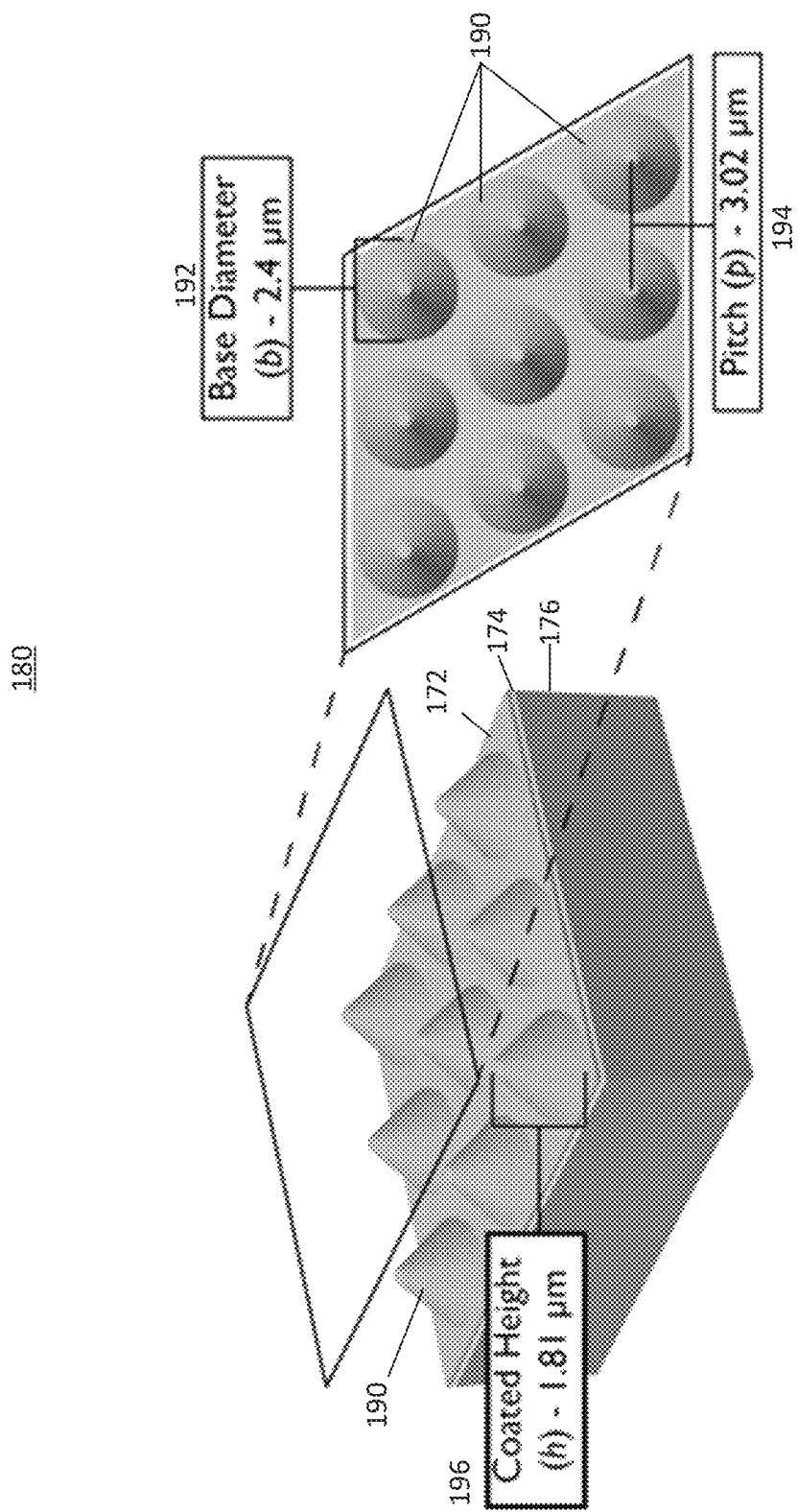
Figure 8B:
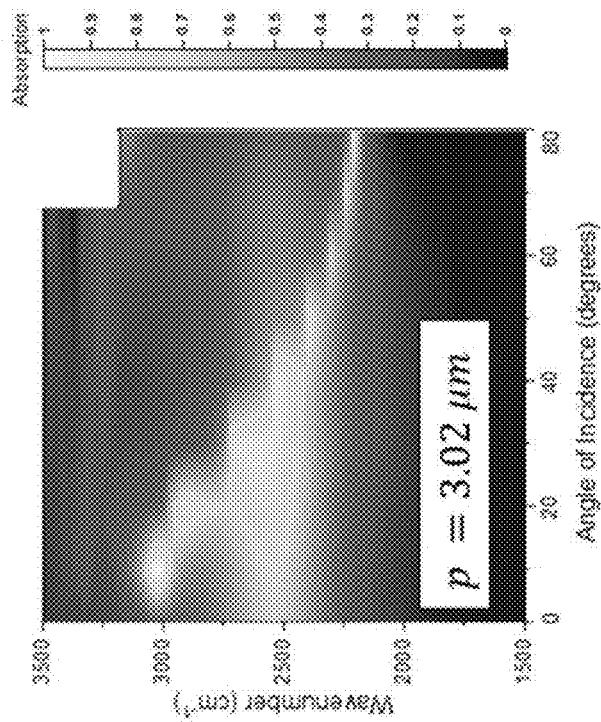
Figure 8A:
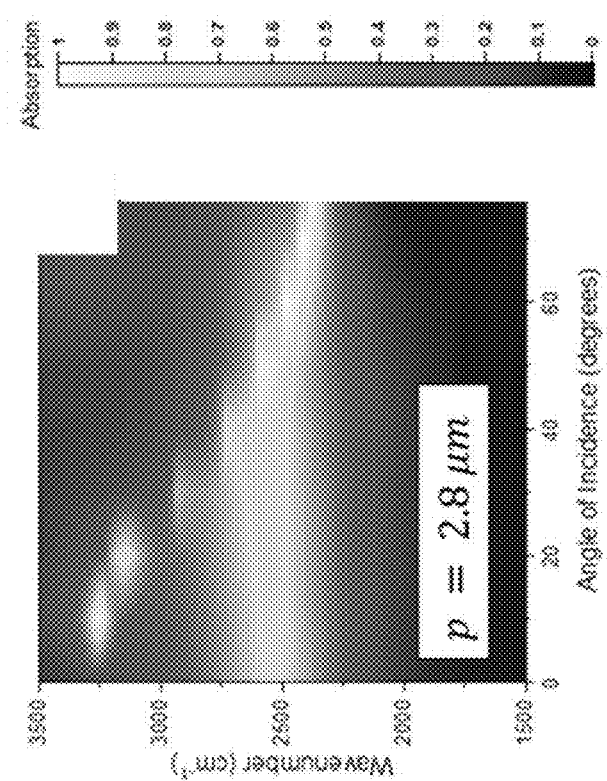
Figure 8C:
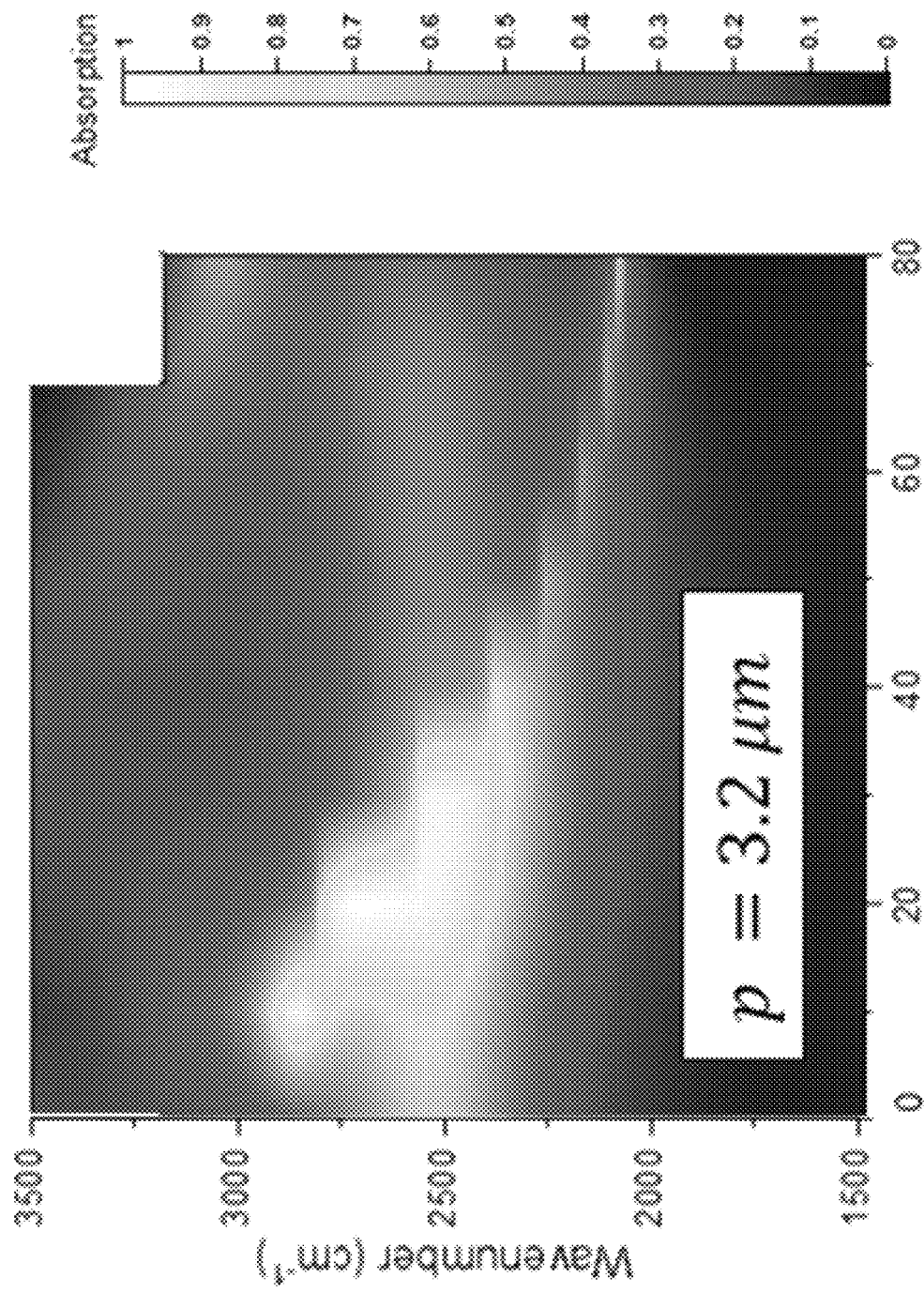
Figure 8D:
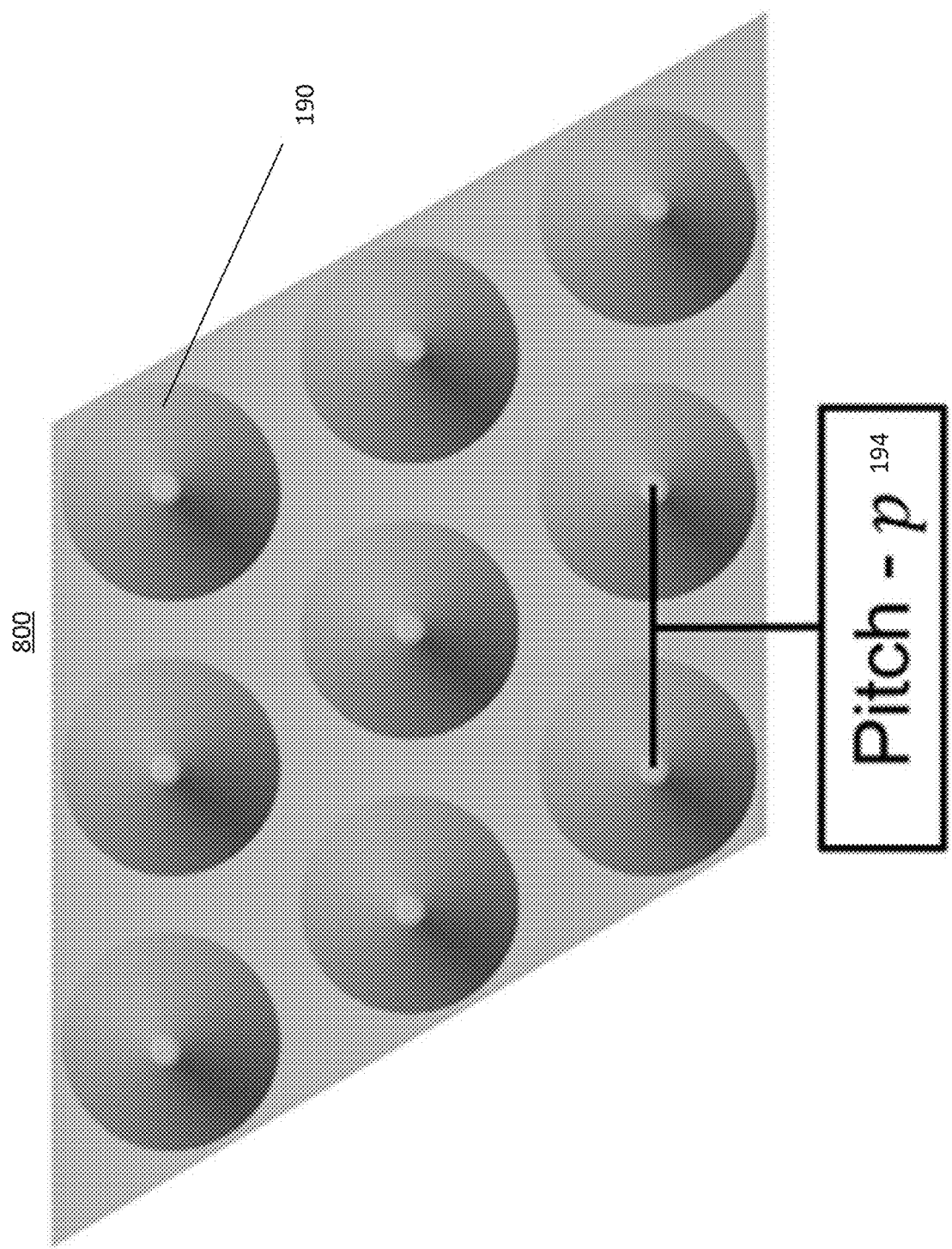
Figure 8E:
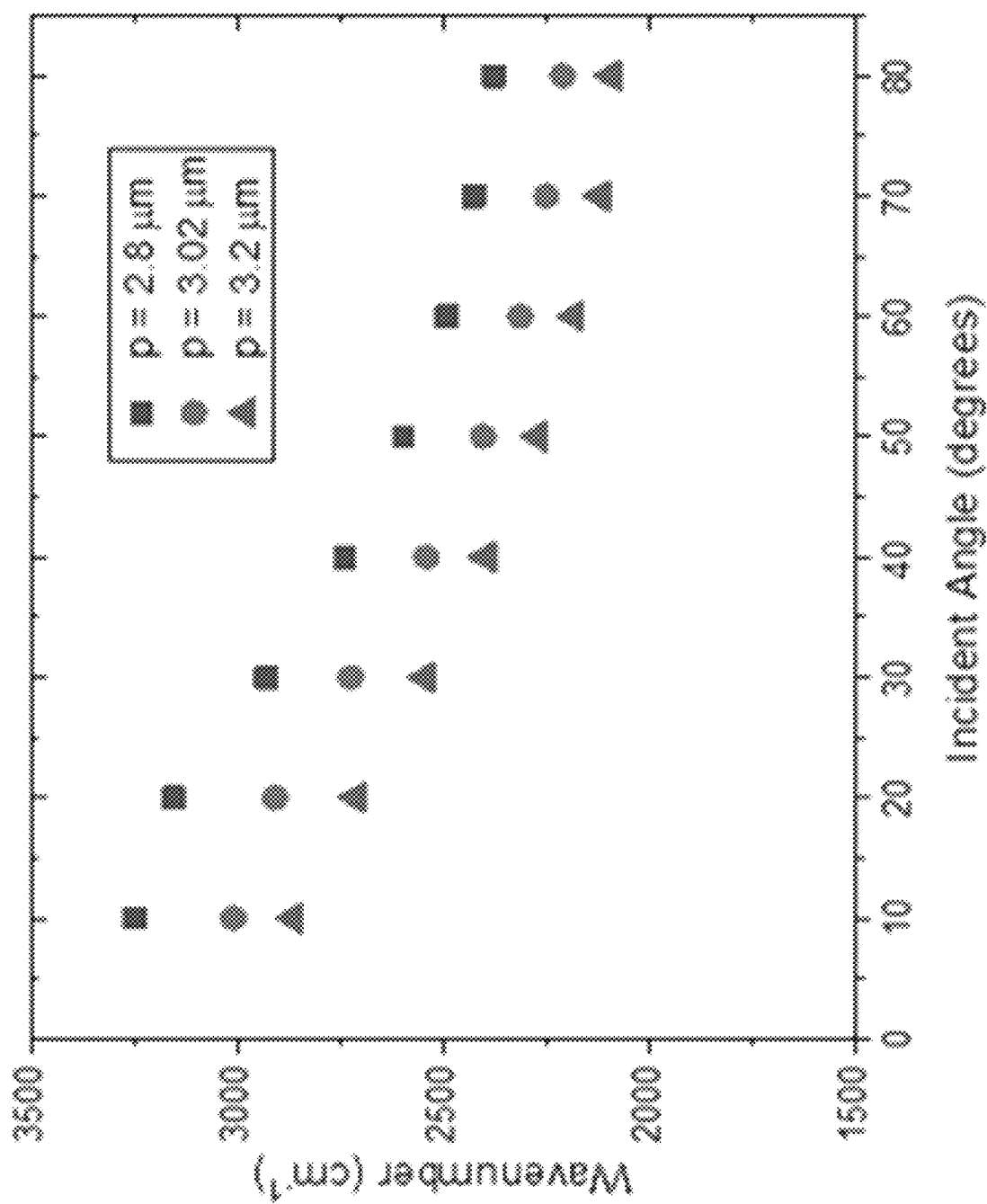
FIG. 8E illustrates the spectral dispersion of diffractive mode for the three pitch values whose simulated angle-dependent p-polarized absorption is shown in FIGS. 8A-8C.

A schematic of an example coated PSS structure 180 is shown in FIG. 1D. The example PSS structure 180 can be used as part of the narrowband emitter 160 described with reference to FIG. 1B. The PSS can include any number of cones 190 formed on the surface of the PSS. The cones 190 can be coated with a CdO film 172 and an Au layer 174, as described with reference to FIG. 1C. The geometry of the cones 190 can be tuned to affect the emission of the narrow band emitter including the structure 180. In the non-limiting example shown in FIG. 1D, the base diameter 192 of the cones 190 is 2.4 µm, the pitch 194 of the cones is 3.02 µm, and the coated height 196 of the cones is 1.81 µm. FIG. 8D illustrates a top-down view 800 of cones 190 including the pitch 194

Figure 11A:
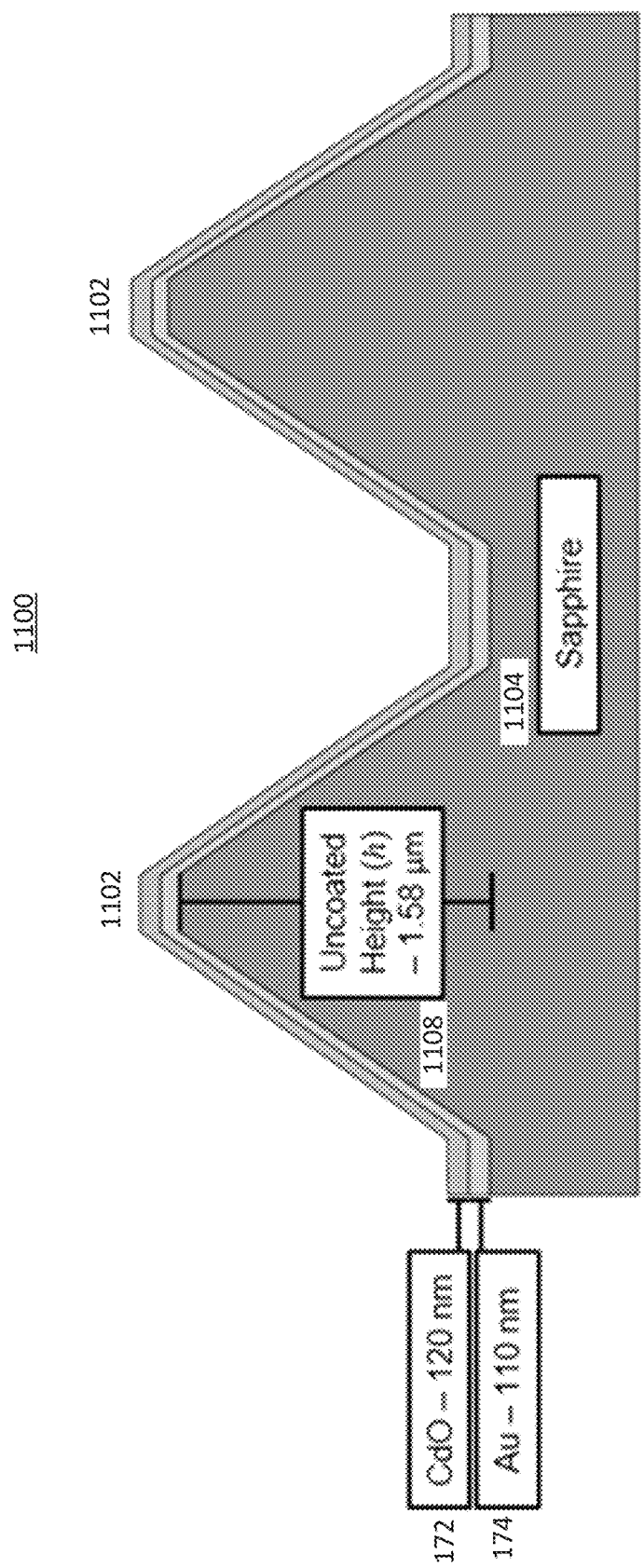
Figure 11B:
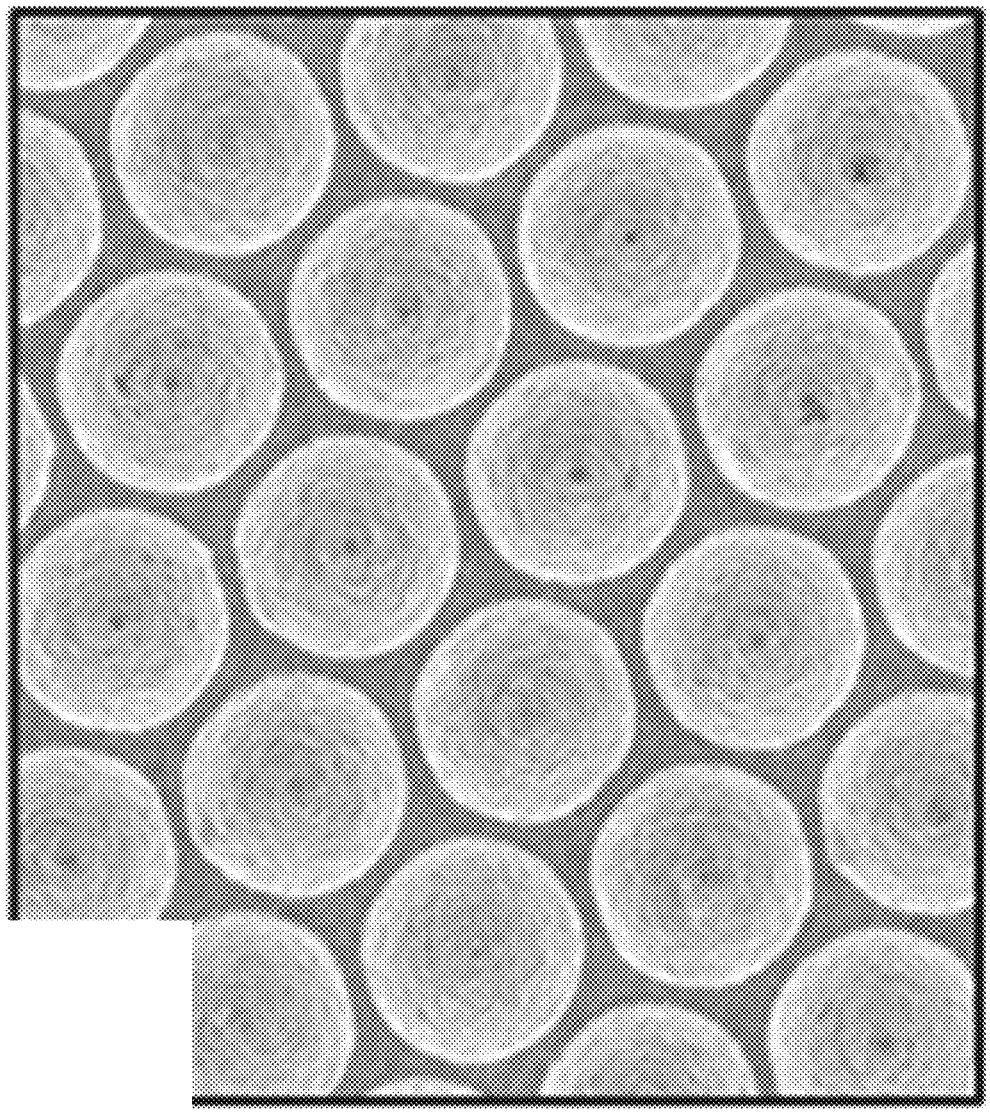
Figure 11C:
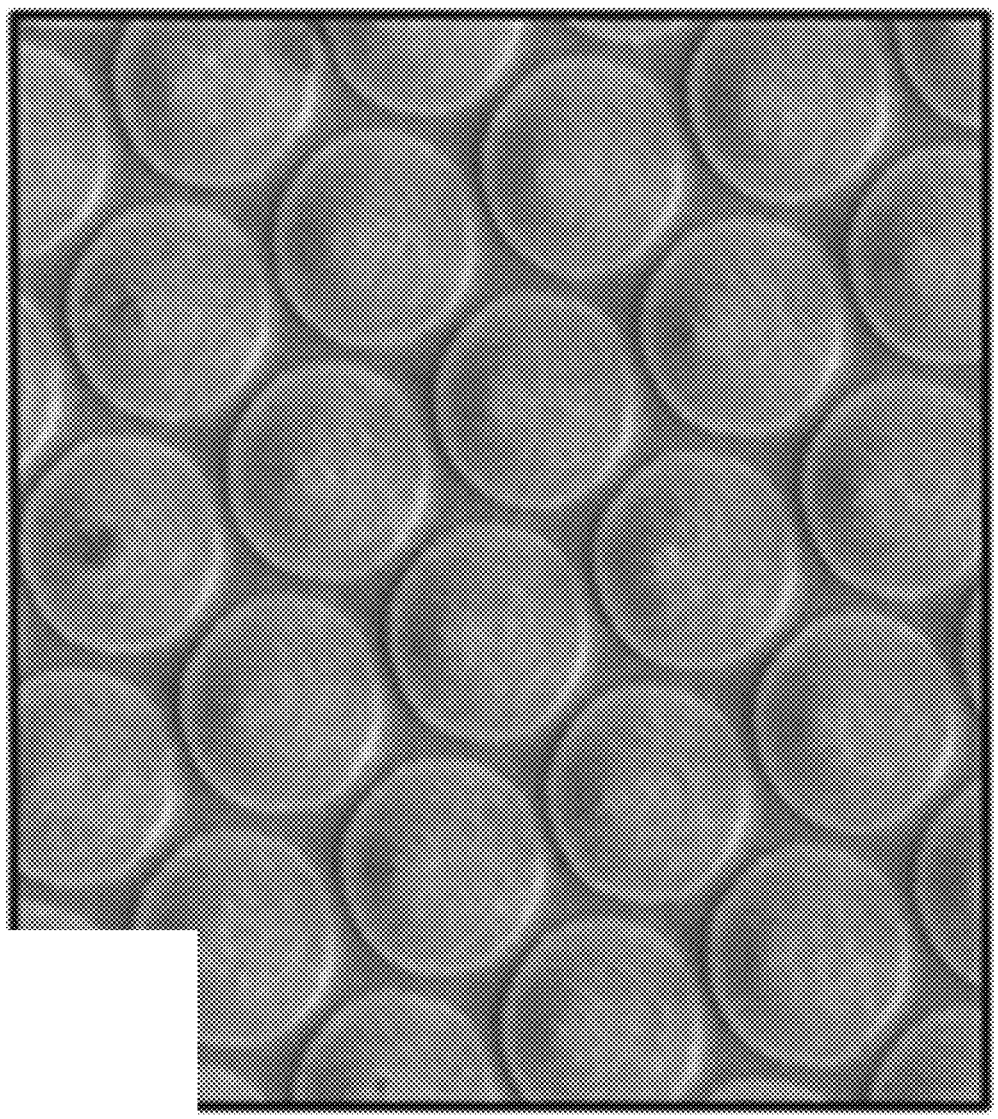

FIG. 11A-11C illustrate film geometries, where: FIG. 11A illustrates a cross sectional view including cone heights and thicknesses; FIG. 11B illustrates a cone geometry viewed from normal incidence; and FIG. 11C illustrates cone geometry viewed from 22° angle of incidence. FIG. 11A, illustrates a cross sectional view 1100 of cones 1102 that can be used in embodiments of the present disclosure (for example, as the cones 190 shown in FIG. 1D). The cones 1102 are formed from the PSS 1104, and are coated with CdO film 172 and Au layer 174. As shown in FIG. 11A, the geometry of the cones 1102 can be affected by the thicknesses of the CdO film 172 and the Au layer 174. The uncoated height 1108 of the PSS 1104 is shown in FIG. 11A.

It should be understood that the dimensions and proportions shown in FIG. 1D are only non-limiting examples, and that the dimensions and proportions can be varied to affect the properties of the narrowband emitter. The source center wavelengths can be spectrally tuned from approximately 2-9 µm free-space wavelengths (5,000-1,111 cm$^{-1}$) in CdO via doping [23-25], allowing these devices to target essentially the full fingerprint region. Similarly, narrowband single and multifrequency thermal emission has been demonstrated in ultrathin, Berreman-mode-supporting CdO films and multilayer stacks, respectively. [26]. However, in flat films these Berreman excitations couple only to p-polarized light and exhibit highly off-normal angles of emission, with the emissivity peaking near the Brewster condition (~65°). By growing the ENZ CdO film upon a PSS, the thermal emission is no longer restricted to angles around the Brewster angle, instead emitting over all angles, with the strongest emission occurring around the surface normal. Further, the cylindrical symmetry of the PSS cones allows for the out-coupling of both s- and p-polarized thermal emission. While the periodicity of the PSS structuring does induce some angular dispersion in the spectra, this is primarily observed at the steepest angles, and thus induces minimal influence upon the NDIR response normal to the surface.

Embodiments of the present disclosure also include methods for performing non-dispersive infrared (NDIR) sensing. FIG. 14 illustrates a method 1400, according to an example embodiment of the present disclosure. At step 1402, the method 1400 includes selectively emitting, by a nanophotonic infrared emitting metamaterial (NIREM) emitter, radiation corresponding to a respective vibrational resonance frequency of each of a plurality of different analytes of interest.

At step 1404, the method 1400 includes detecting, by a broadband detector, photons associated with vibrational activity of the analytes of interest in response to the emitted radiation.

In some embodiments, the method 1400 further includes determining, based on the photon detection, one or more properties of the analytes of interest. A non-limiting example of a property of the analyte of interest is the concentration of the analyte of interest.

The method 1400 can be performed using the devices described throughout the present disclosure, for example with reference to the devices 100 and 150 described with reference to FIGS. 1A and 1B, respectively. Additionally, as described throughout the present disclosure, the analyte of interest can be $CO_2$ in some embodiments of the method 1400.

In some embodiments of the method 1400, different emitters from the NIREM emitter can be activated during different time periods so that the NIREM emitter emits radiation corresponding to vibrational resonance frequencies of different analytes of interest at different times. As a non-limiting example, at a first time, or during a first time period, a first emitter can be activated to emit radiation corresponding to the vibrational resonance frequency of a first analyte of interest. And, at a second time, or during a second time period, a second emitter can be activated to emit radiation corresponding to the vibrational resonance frequency of a second analyte of interest. The first time and second times can be different, and the first analyte of interest and second analyte of interest can also be different.

It should be understood that embodiments of the method 1400 can be performed using any of the devices described herein. For example, in some embodiments, the emitters used at step 1402 to selectively emit radiation can be arranged in an array. Alternatively or additionally, the NIREM emitter used in step 1404 can include a PSS. Optionally the PSS includes a CdO film supporting an ENZ/Berreman optical mode. In some embodiments, the NIREM emitter can be configured for for s-polarized thermal emission and/or p-polarized thermal emission.

As additional non-limiting examples, in some embodiments of the present disclosure the detector used at step 1404 can be a thermopile.

Experiments described herein illustrate the detection of $CO_2$ using an NIREM device demonstrating similar sensitivity to that of a broadband emitter and narrow bandpass filter used in a standard NDIR detector. This can enable the elimination of the bandpass filter as well as offering the opportunity to realize next generation devices offering multi-frequency detection (through depositing multiple films on the same sample, or multiple die combined into a single NDIR architecture) within the same gas cell. These experiments are intended as non-limiting examples that illustrate the potential for the NIREM devices as a direct replacement IR source for the broadband emitter in conventional NDIR devices, however other applications are contemplated, including the use of NIREM devices to detect gases other than $CO_2$.

Figure 6:
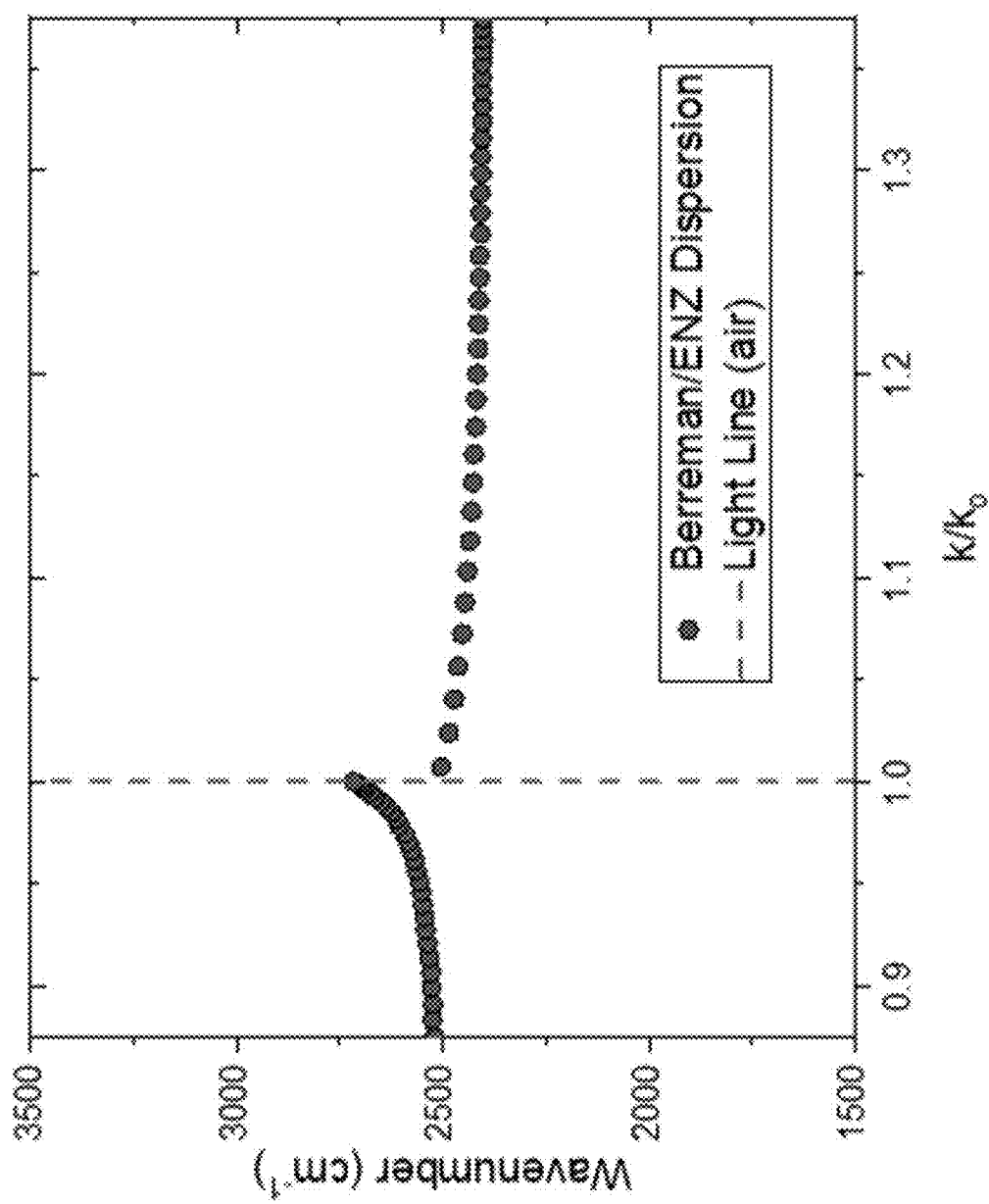
FIG. 6 illustrates Berreman/epsilon-near-zero (ENZ) dispersion calculated using Transfer-Matrix-Method [37] calculation of a 120 nm thick CdO film. As the Berreman mode approaches the light line from the left, a blue shift is observed, resulting in a slight blue shift at highly off-normal angles (80°) in the thermal emission spectra from the flat film samples, as shown in FIG. 2A and FIG. 7D.
Figures 7A, 7B:
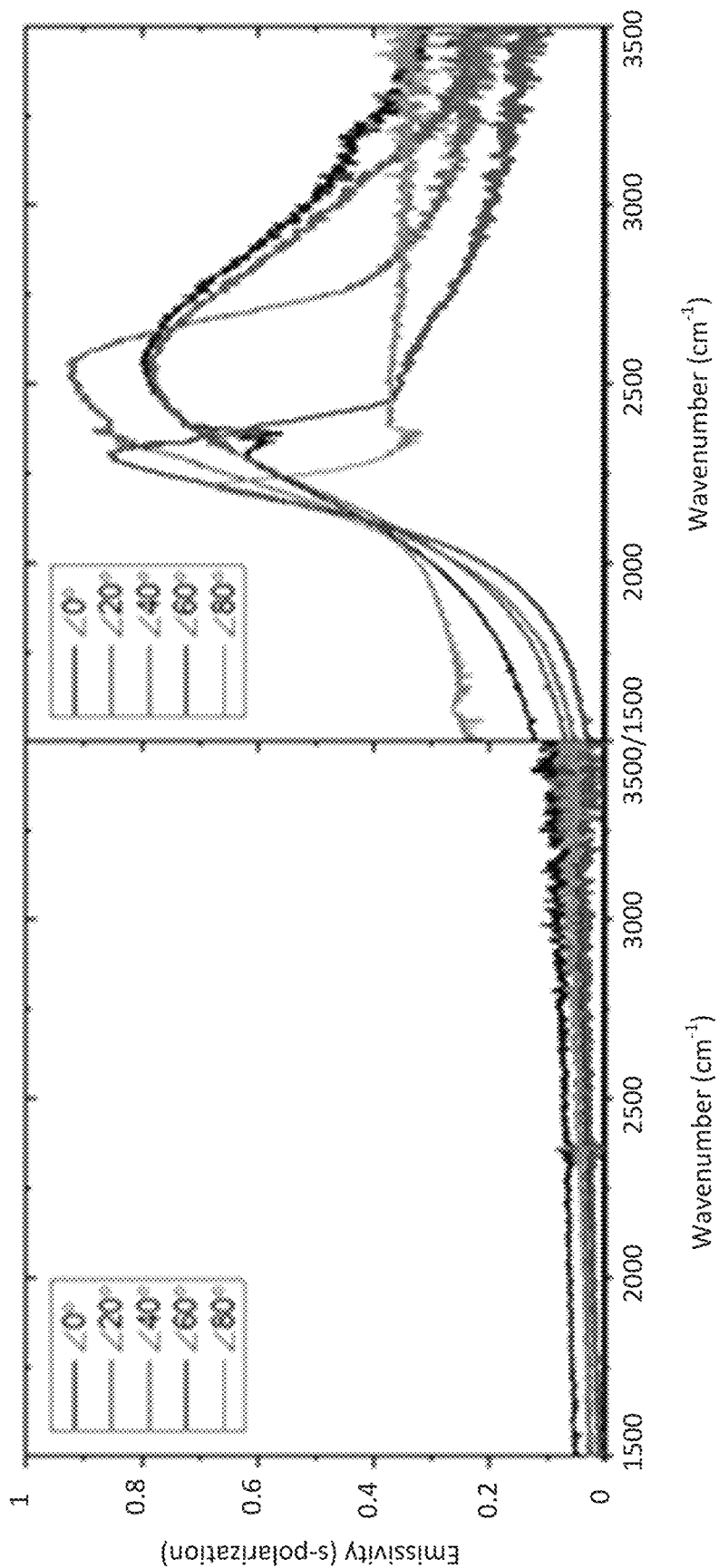
Figures 7C, 7D:
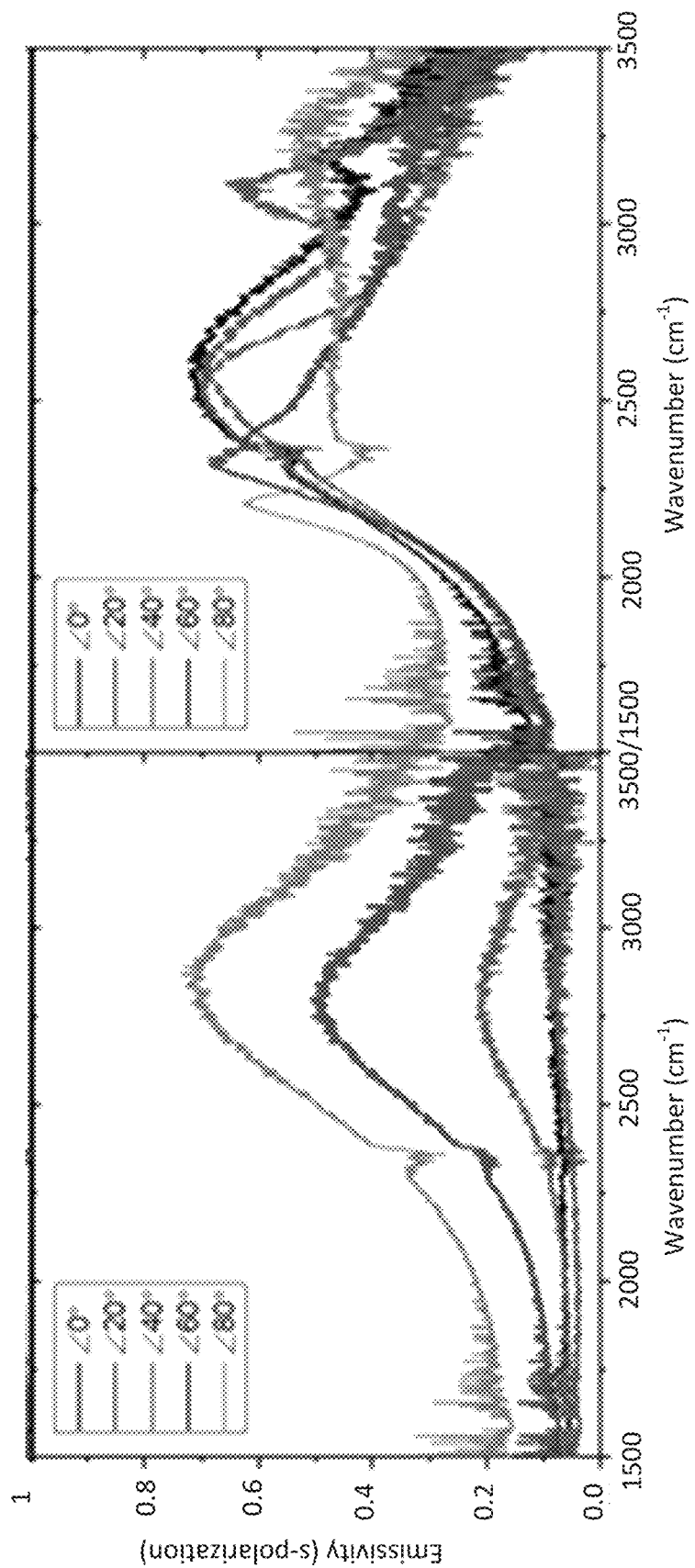
Figure 7F:
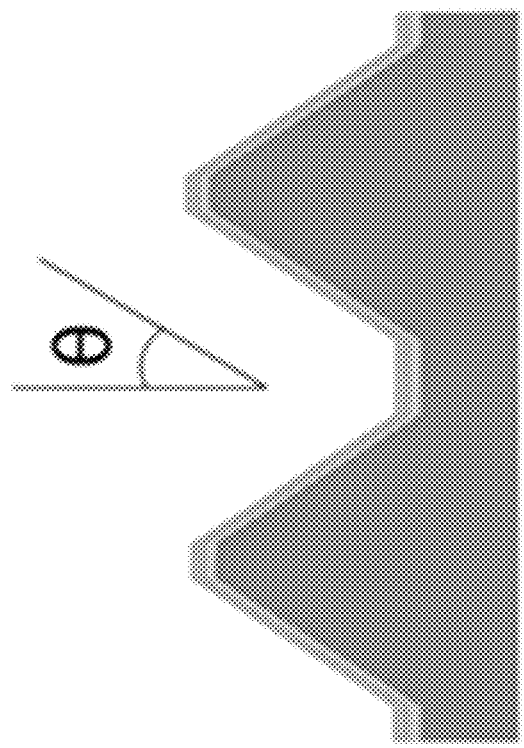
Figure 7E:
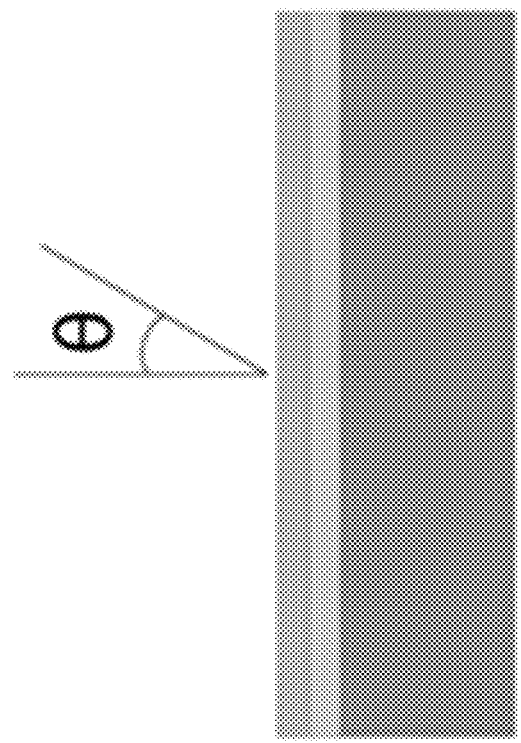

The ENZ dispersion exists outside of the free-space light cone, requiring auxiliary momentum in order to be accessed. The calculated Berreman/ENZ modal dispersion is shown in FIG. 6. Embodiments of the present disclosure produce strong emission, and therefore (through Kirchhoff's law) strong absorption, from such a 120-nm thick film of $N_d$=5.8×10$^{19}$ cm$^{-3}$ In:CdO film that is derived from this dispersion relation, as described herein. The experimentally measured and numerically calculated emission from the thin film CdO are shown in FIGS. 2A and 2C, respectively. As the emission spectra provided in FIG. 2A is unpolarized, an emissivity at close to 0.5 implies near-unity absorption of p-polarized light through Kirchhoff's law, at an angle of approximately 70°. The polarized thermal emission spectra is shown in FIG. 7. For some NDIR applications, steep emission angles wherein the majority of the light can be emitted towards the gas cell wall, rather than being directed towards the detector, adjustments can be made to account for this off-normal emission from the flat film, such as the incorporation of a wedge to direct the emission towards the detector. However, some adjustments can reduce the collected power and/or require high numerical aperture collection optics to overcome. Furthermore, the possible collected power is still limited to below 50% as the Berreman mode only couples to p-polarized light. Thus, for the NDIR application an alternative device design can be required if such challenges are to be overcome.

To enable strong thermal emission of both p- and s-polarized light, designs exploiting different types of physics have been employed. One method broadly implemented in the perfect absorber geometry is to utilize a cross-shaped polaritonic resonator, whereby each arm of the cross can couple to the orthogonal polarization states. When combined with a dielectric spacer and metallic back plane, perfect absorption can be realized. [18,19]. This geometry was utilized by Lochbaum et al. [3] for demonstrating a narrowband emitter and detector for an advanced NDIR scheme. However, as noted above, for such structures to provide polaritonic resonances in the mid-IR, advanced lithographic tools and typically costly plasmonic metals are required. Alternatively, one could envision realizing nanostructures through growth of a polaritonic medium on a periodically textured surface. However, this approach has not been employed for such a device due to the challenges associated with epitaxy on such a non-planar surface. This can result in an increase in defect density and a propensity to form polycrystalline, rather than single crystal epitaxial films, which in turn result in increases in optical loss. Here, CdO offers substantial benefits as it has been previously demonstrated that for highly doped CdO ($>1 \times 10^{19}$ cm$^{-3}$) increases in doping density result in an increased effective mass, while also maintaining the large electron mobilities ($\mu$>300 cm$^2$/V–s) and thus reductions in optical losses, even at significantly elevated carrier densities in excess of $3 \times 10^{20}$ cm$^{-3}$. [27] Furthermore, this material offers a propensity for high-quality growth via high power, impulse magnetron sputtering (HiPIMS) on a variety of substrates, including non-planar structures and metal films while maintaining the low loss tangents that highlight the promise of this material. [23,24]

Figure 3A:
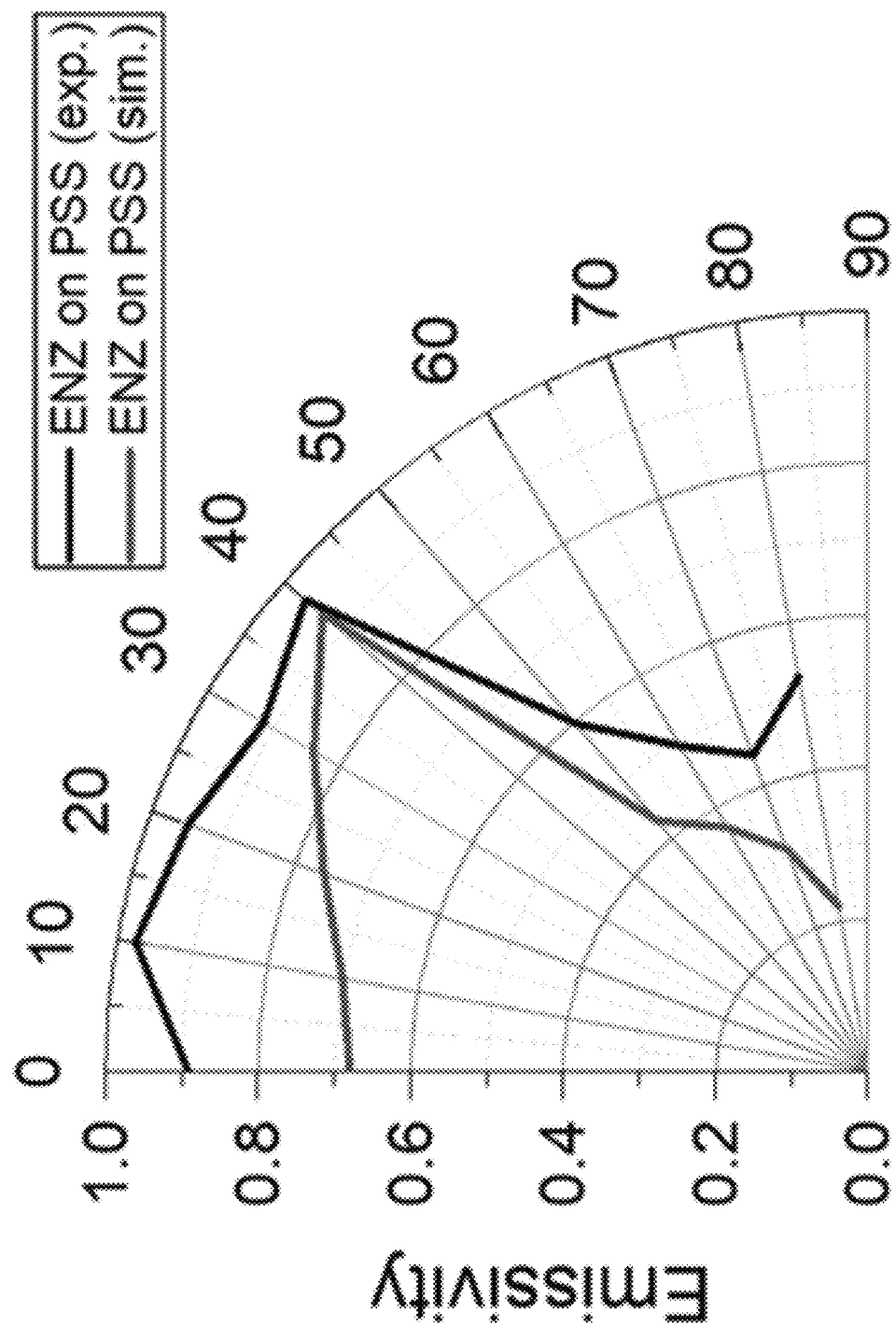
Figure 3B:
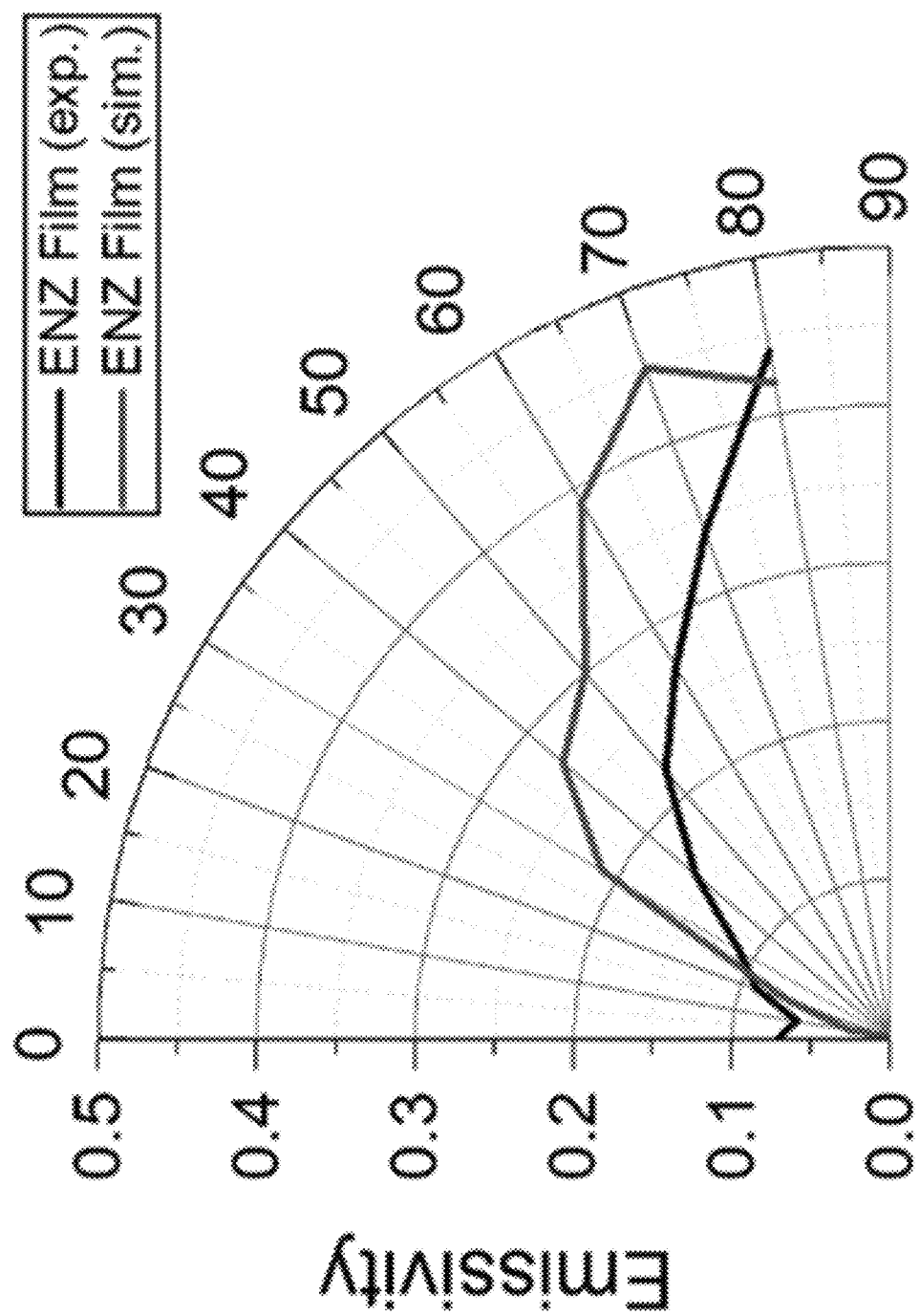

For low cost NDIR sensors, the structured surface can be one that is created via scalable, low cost methods on large area substrates. PSSs offer such a substrate as the structured surface is the result of wet chemical treatment in $H_2SO_4$ at elevated temperatures (~240° C.) as well as dry etching methods, and are commercially available at up to 8-inch wafers at low cost. For the purpose of testing the spectral and spatial emissivity of an ENZ CdO film when grown on such a PSS substrate, a 120-nm thick n-type In:CdO film was grown via HiPIMS on a PSS substrate which had been first coated with a 110 nm thick sputtered gold layer. A schematic of the PSS cone cross section along with scanning electron microscope (SEM) images of the coated structure are provided in FIG. 11. Note that the layer thicknesses and stacking order are identical for the CdO flat film and PSS samples. The PSS substrates used consisted of a periodic array (pitch p=3.02 µm) of circular-base (b=2.4 µm) conical structures with an uncoated height of 1.58 µm. A top-view schematic of the gold and CdO coated structure is depicted in FIG. 1D. In contrast to the flat Berreman/ENZ film (FIGS. 2A and 2C), when the same film is grown on the PSS, several significant modifications are realized (FIGS. 2B and 2D, respectively). First, as described above, the structuring of the film results in near-unity emissivity (absorptivity) at near-normal incidence up to approximately 40° off-normal (FIG. 3B). The symmetric, conical shape of the structures enables out-coupling of both p- and s-polarized light on resonance with high efficiencies. Additionally, as the angle is increased away from the surface normal, a significant narrowing of the resonant mode is observed due to interference between the dispersive diffractive and non-dispersive ENZ resonant modes as can be seen in FIG. 2B as well as the contour plot in FIG. 3C. The slight difference in emission frequencies between the flat film and PSS sample is a result of the Berreman/ENZ origin of these modes. Due to the anti-crossing at the intersection [21] of the plasma frequency and light line in air (as shown in FIG. 6) the Berreman mode is excited slightly above and ENZ is excited slightly below the plasma frequency in polaritonic films, with the magnitude of this shift being dependent upon the film thickness. The resonant frequencies are therefore slightly offset from the plasma frequency, but in opposite directions spectrally. These angle-dependent thermal emission measurements were performed using a motorized, rotating thermal emission rig that was built in-house. The measured baseline emissivity is slightly elevated at high emission angles (80°), which is due to the collection of the emission from the hot plate behind the sample. At these large emission angles the spot size (5 mm) was slightly larger than the projection of the sample. A detailed description of the FTIR thermal emission measurements is provided below.

Figure 3C:
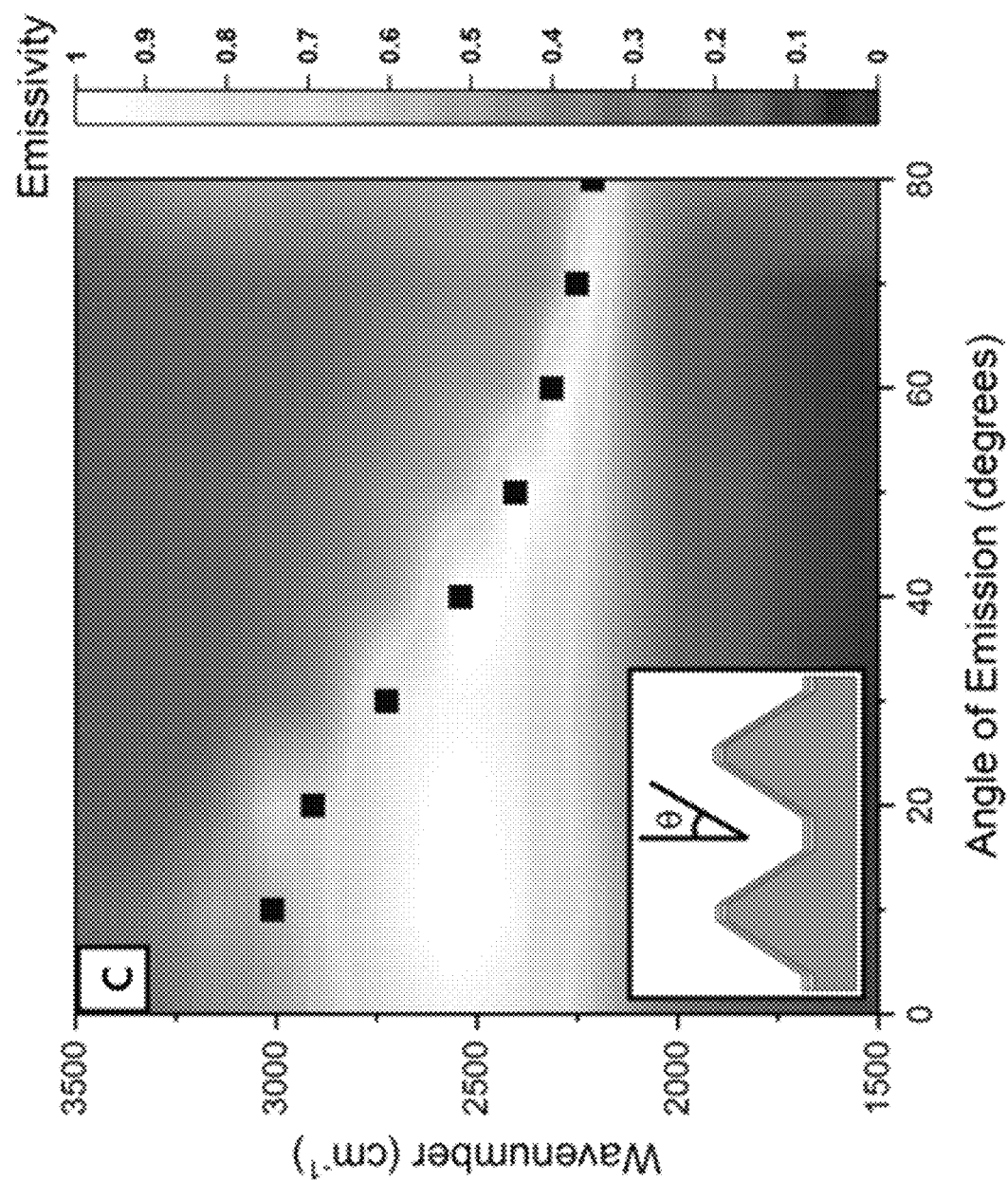
Figure 3D:
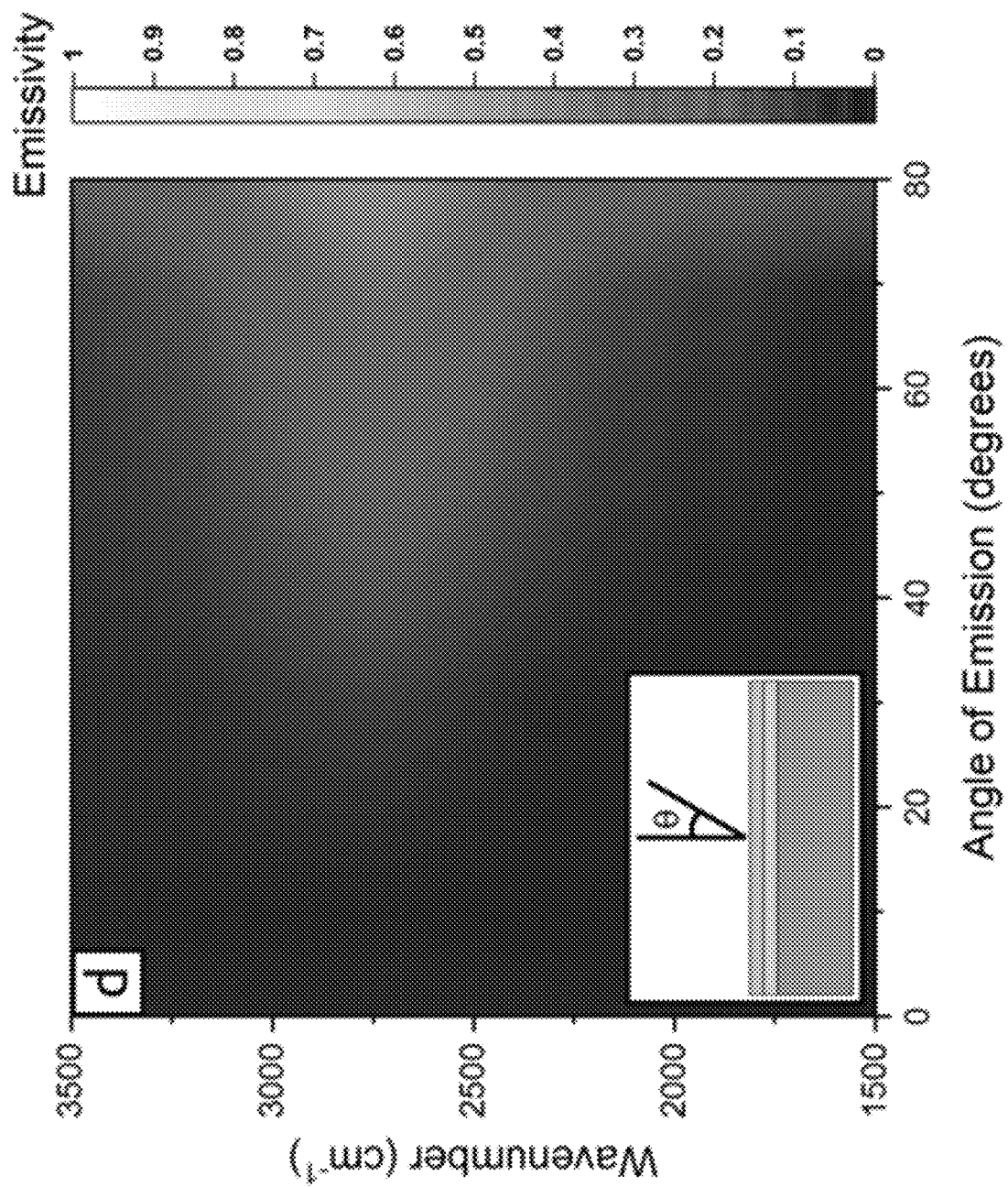

The origin of the spectral narrowing is indicative of interference between the ENZ resonant mode and the diffractive mode resulting from the periodic patterning [28-30] of the PSS template. Fano-like interactions have been reported in a broad range of periodic arrays of polaritonic resonators. [31-34]. To validate this claim, three-dimensional, finite element method electromagnetic simulations of the ENZ CdO layer on a PSS substrate were performed using CST Studio Suite. Here a dielectric function model previously reported [25] and the sample geometry presented in FIG. 1D were implemented in order to determine the angle-dependent absorption spectra displayed in FIG. 2D. Calculations of the angle dependent absorption of the structure (FIG. 2D) agree well with the experiments performed (FIG. 2C). From FIGS. 2B and 2D it can be seen that the dispersive, diffractive mode effectively tunes through the ENZ polariton resonance, which maintains a nominally constant frequency, granting no indication of modal strong coupling. Note again that due to Kirchhoff's law, these absorption spectra can be compared directly to the measured angle-dependent emissivity spectra. The simulated spectral position of the diffractive mode is included as black squares overlaying the measured emissivity contour plot as shown in FIG. 3C showing excellent agreement between measured and simulated values.

Figure 4B:
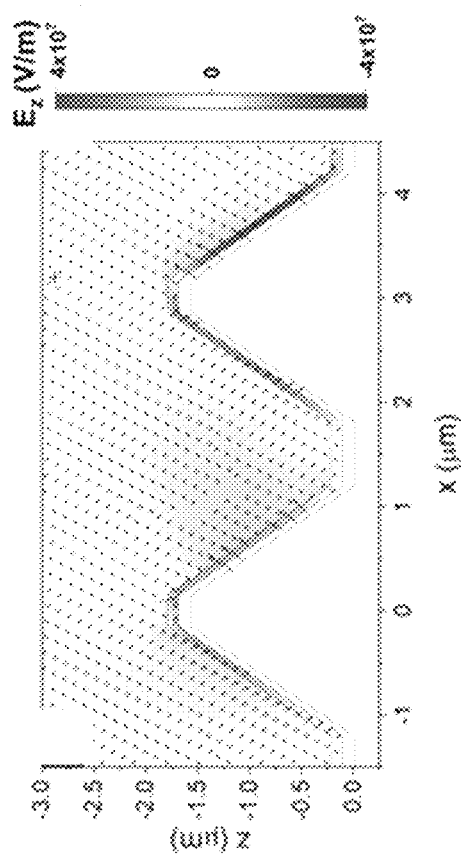
FIGS. 4A-4B illustrate field profiles simulated at a 20° angle of incidence.
Figure 4A:
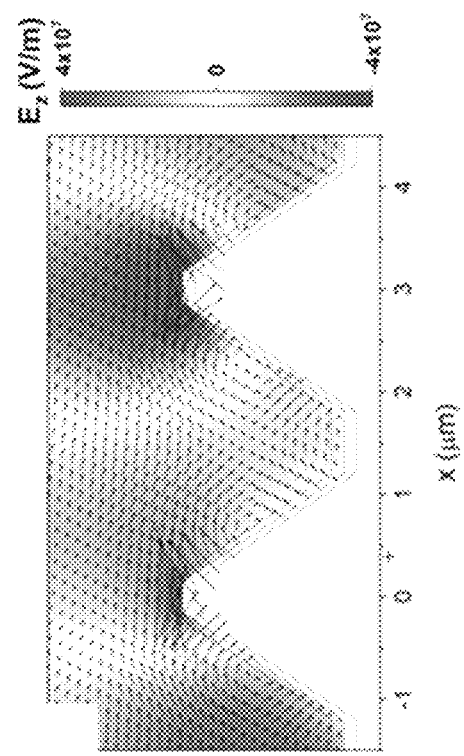

The origin of these resonant features as diffractive in nature is confirmed through comparison of the spectral dispersion at different grating pitches, with the diffractive mode shown to redshift as the pitch is increased as shown in FIG. 8. Additionally, cross-sectional field profiles of the z-oriented electric field ($E_z$) as well as the Poynting vector ($\vec{P}$) at the ENZ condition (2550 cm$^{-1}$) and at the peak of the diffractive order for angles of 20° (3000 cm$^{-1}$) are illustrated in FIGS. 4A and 4B, respectively, showing distinctly different resonant behavior. At the ENZ resonance shown in FIG.

Figure 9:
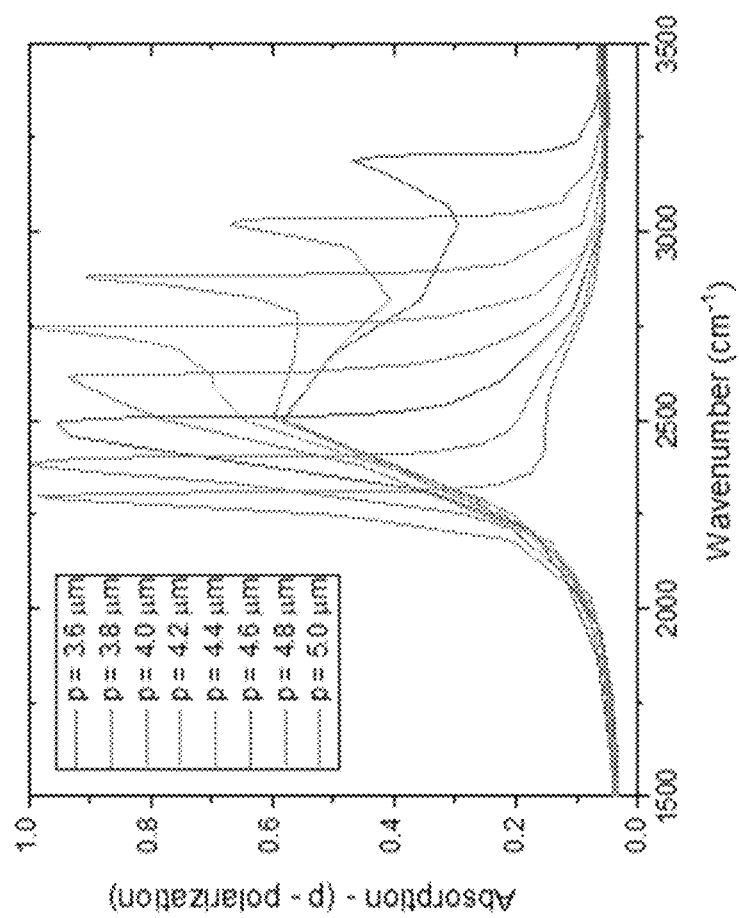
FIG. 9 illustrates simulated absorption spectra detailing the pitch dependence at normal incidence for the CdO on PSS sample. As the pitch is increased and diffractive mode redshifts through the ENZ mode, the interference effect leads to a reduction in absorption linewidth.
Figure 10:
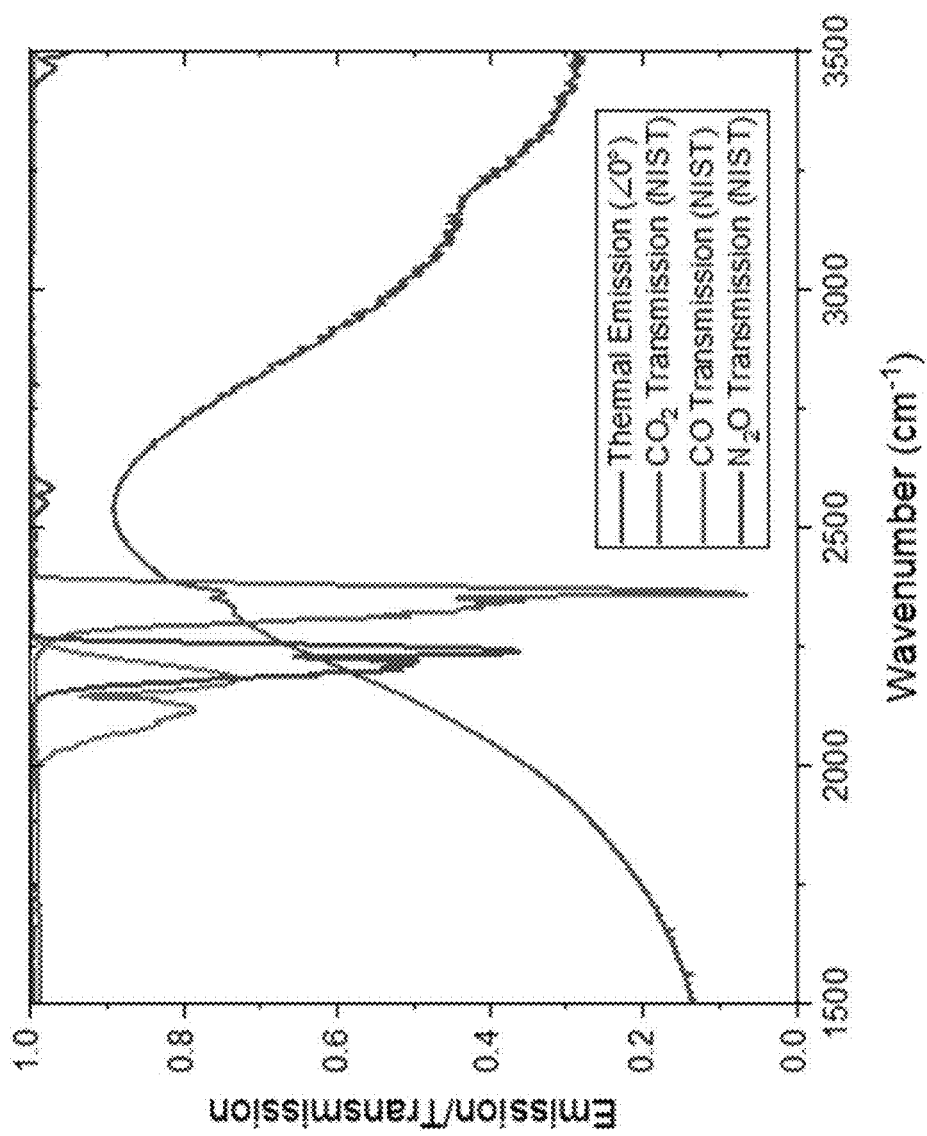
FIG. 10 illustrates normal (0°) thermal emission from the CdO on PSS sample, showing spectral overlap with $CO_2$, $N_2O$, and CO absorption. [38].

4A, a strong confinement of the electromagnetic fields within the ENZ layer is observed, with a clear dipolar character in the phase across the resonant structure. Further, the magnitude of P is relatively small ($|P_{max,ENZ}|=3.3\times10^{12}$ W/m$^2$) both inside and outside of the CdO layer, with an orientation matching that of the incident wave. However, at the diffractive order, the mode is identified as having a strong in-plane momentum, as indicated by the alignment and magnitude of $\vec{P}$ ($|P_{max,Diff}|=7.0\times10^{13}$ W/m$^2$) above the sample, and fields coupled between adjacent resonators consistent with a diffractive mode. However, while the presence of the diffractive modes induces some angular dispersion in the spectral emissivity, this is predominantly at steep angles in the spectral region of interest ($\omega\approx2550$ cm$^{-1}$), and thus, at angles within +/−40° off normal the emission spectra is still peaked at the ENZ condition with near-unity emissivity as shown in FIGS. 3A and 3C). As described herein, this diffractive order can be tuned spectrally by depositing an identical CdO film on a PSS of a different pitch. Alternatively, the plasma frequency of the CdO film can be adjusted via doping to achieve the match for a given substrate pitch, at higher/lower frequencies. Thus, it is possible to design a CdO on PSS structure in which the grating resonance is non-interacting with the ENZ emission at larger off-normal angles or overlapping with the ENZ resonance at normal incidence as is shown in FIG. 9.

Based on the near-unity, narrow bandwidth thermal emission resulting from the CdO PSS structure, and the redirection of both p- and s-polarized light within a radiation pattern directed at angles within 40° of the surface normal, it is clear that there is a high potential for this CdO-based NIREM device for advanced NDIR approaches. This was validated by implementing the external thermal emission input of a Bruker Vertex 70v FTIR spectrometer, integrating the thermal emission (250° C.) from the CdO-PSS device at the surface normal as the source. This was passed through the interferometer and a short-path gas cell from Pike Technologies and detected using the MCT/A detector. The sample compartment, which housed the gas cell, was kept under N$_2$ purge, whereas the rest of the FTIR was evacuated. Once the sample compartment and gas cell were adequately purged, CO$_2$ gas was passed through the gas cell using calibrated gas cylinders with 400 and 50 ppm of CO$_2$ in N$_2$. To enable direct comparison with a more traditional blackbody-based NDIR approach, these results were compared with similar measurements performed using a vertically-aligned carbon nanotube (VACNT) array blackbody (Nano-TechLabs, Inc.) reference as the source. Further details regarding the gas cell measurements are described below.

Figure 5:
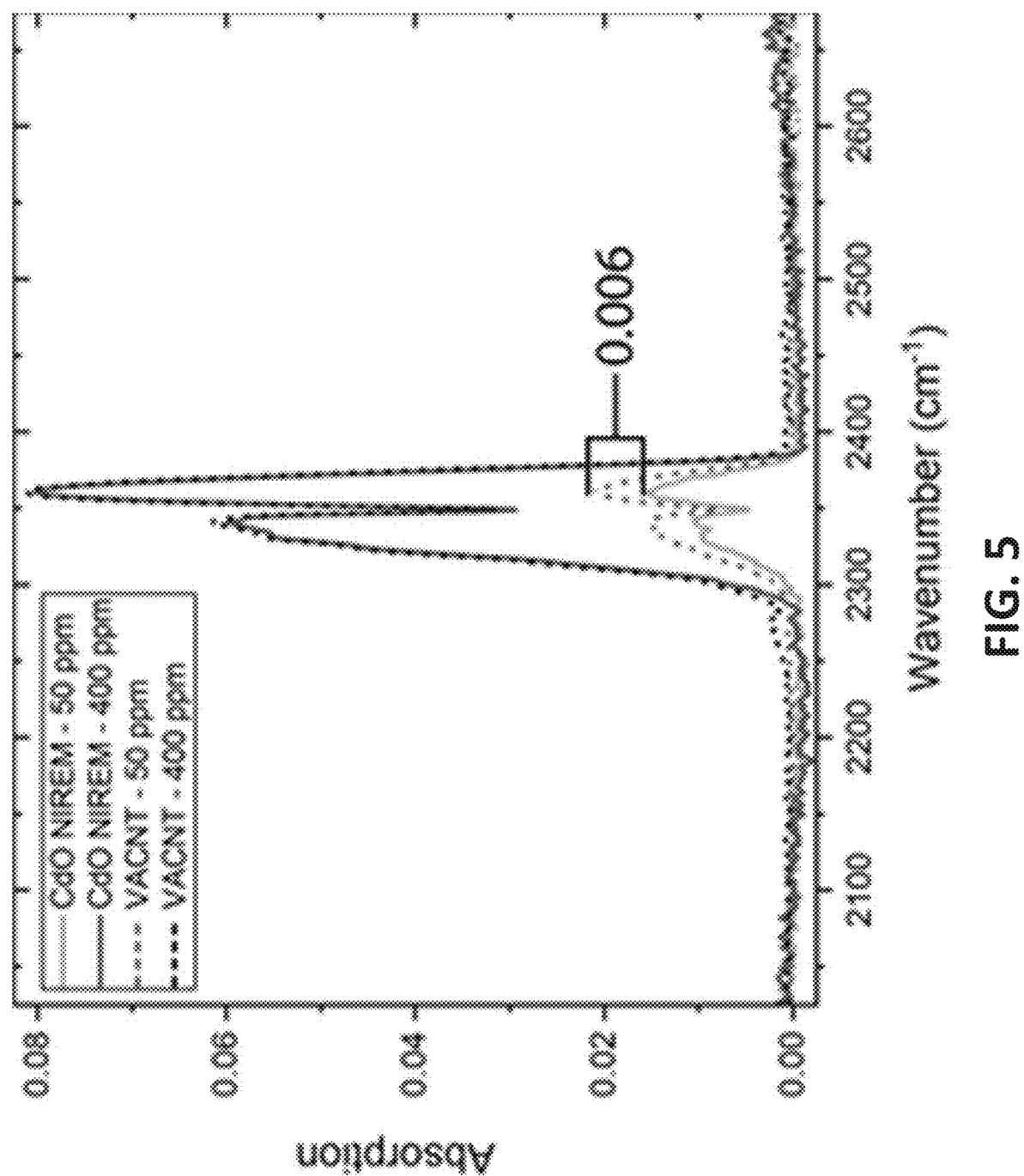
FIG. 5 illustrates absorption spectra with the source at 250° C. The performance of a CdO on PSS narrowband emitter according to one embodiment of the present disclosure is compared to a blackbody at $CO_2$ concentrations of 400 and 50 ppm. The performance of the embodiment of the present disclosure illustrated in FIG. 5 is comparable to the blackbody sample even at low CO2 concentrations (50 ppm).
Figure 13:
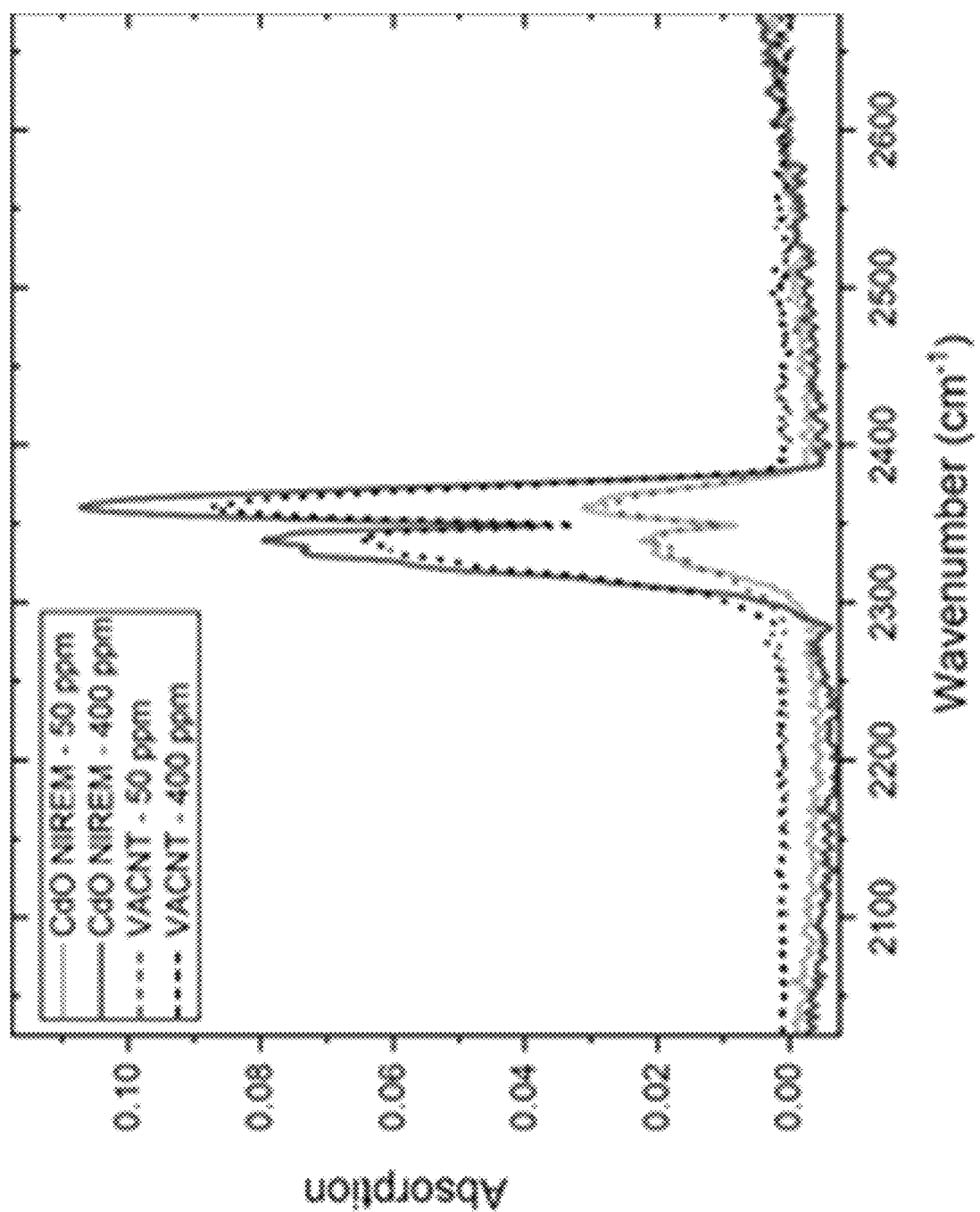
FIG. 13 illustrates absorption spectra with the source at 200° C., comparing the performance of an embodiment of the present disclosure including a CdO on PSS narrowband emitter to a blackbody at $CO_2$ concentrations of 400 and 50 ppm. The embodiment of the present disclosure including a narrowband emitter is shown to outperform the blackbody sample at 400 ppm and performs comparably to the blackbody sample at low $CO_2$ concentrations (50 ppm).

The mid-infrared spectrum of CO$_2$ consists of two molecular vibrational modes corresponding to the antisymmetric stretching modes at 2349 cm$^{-1}$ and 3756 cm$^{-1}$. [35] As the collected spectra from the NIREM device is peaked at 2550 cm$^{-1}$, with a radiation pattern suitable for directing the light towards the detector, this device can be suited for sensitive detection of CO$_2$, targeting the absorption at 2349 cm$^{-1}$. Using the experimental setup outlined above, and further detailed below, the sensitivity of the NIREM device was validated. The NIREM device demonstrated similar sensitivity to CO$_2$ gas at both 50 and 400 ppm as a blackbody spectrum as shown in FIG. 5. Even at the lowest concentration of the CO$_2$ calibration gas that was commercially available (50 ppm), the NIREM device still detected over 1.5% absorption in this experiment. This would imply that with this non-optimized geometry that over an order of magnitude further reduction in CO$_2$ concentration should still be detectable in a 15-cm cell. From this comparison it is clear that although the CO$_2$ absorption at 400 ppm is equivalent for both sources, at 50 ppm it is slightly suppressed for the NIREM source, differing by just under 0.6% which falls within the error of the measurements. Although these measurements were performed under N$_2$ purge there is a possibility of background CO$_2$ fluctuations that can cause slight deviations in the absorption magnitude. Similar performance was observed from the NIREM device to the VACNT sample in CO$_2$ absorption measurements at 200° C. as shown in FIG. 13, demonstrating the temperature stability in the performance of the NIREM device. As described above, ~200 cm$^{-1}$ spectral detuning of the NIREM emission center frequency from the CO$_2$ absorption occurred. With further optimization of the ENZ emission frequency with respect to the CO$_2$, an increase in sensitivity could be produced. The spectral linewidth of the NIREM emitter described here is sufficiently broad that some spectral overlap can occur with other gases of interest, for instance N$_2$O. However, the embodiment of the present disclosure used to produce these experimental results is not representative of the narrowest CdO-based ENZ emitter/absorber linewidths, with values as narrow as 321 cm$^{-1}$ having been reported. [36]. For such devices, this overlap would no longer be present and thus the concept of filterless NDIR with embodiments of the simple, low-cost NIREM emitter can be created, and are contemplated by the present disclosure. Furthermore, by implementing more advanced detection schemes, such as differential or modulated spectroscopies, or by further optimizing the ENZ resonance to the center frequency of the CO$_2$ absorption and increasing the PSS pitch to induce a narrowing of the emission linewidths, increased selectivity and potentially sensitivity can be realized.

The growth of n-type In:CdO thin films on a PSS template offers several key advantages over thin flat CdO films discussed previously [26], as the structured surface enables near-unity emissivity of both p- and s-polarized light from the Berreman mode, while redirecting the light from the Brewster angle (~65°) observed for flat films to a radiation pattern featuring >0.9 emissivity throughout the solid angle defined by +/−40° off-normal. This NIREM device therefore offers a narrowband, near-perfect absorber with directional emission suitable for replacement of a broadband blackbody emitter and bandpass filter within NDIR sensor platforms. The periodicity of the PSS template was observed to induce a strong diffractive mode that results in a strong spectral narrowing at highly off-normal emission angles (>40°), however, this was demonstrated to have minimal impact upon the emission peak at the Berreman condition at shallower angles and thus negligible impact upon the performance within an NDIR configuration. The performance of an embodiment of the present disclosure including a NIREM device for such an NDIR application has been validated, and similar sensitivity (when compared to a blackbody currently employed in NDIR technologies) to trace level concentrations (50 ppm) of CO$_2$ gas has been observed. The results described herein therefore imply that such NIREM devices can provide a designer IR source for plug-and-play replacement of the blackbody/bandpass filter combo, significantly reducing NDIR device cost, complexity and potentially extending the functionality. The elimination of the bandpass filter thereby also makes possible multiple NIREM devices within a single die, enabling serial detection of several molecules within the same gas cell, without the need for inclusion of a bulky and expensive filter wheel or multiple NDIR devices. Furthermore, by using this approach, advanced NDIR concepts whereby multiple characteristic vibrational resonance frequencies of more complicated analytes can be detected are contemplated. This can extend the NDIR concept from the current state of the art to the detection of biological and chemical warfare agents, chemical byproducts, or environmental contaminants. As used herein "analyte" can be any chemical or chemical compound that is targeted for analysis, and an analyte can include multiple characteristic vibrational resonance frequencies. The present disclosure contemplates that the analysis of the analyte by embodiments described herein can include detecting more than one of the multiple characteristic resonance frequencies of the analyte.

EXPERIMENTAL RESULTS

In an experimental implementation of an embodiment of the present disclosure, In:CdO was deposited using reactive high power impulse magnetron sputtering (R-HiPIMS) from a metallic cadmium target. Doping was achieved through RF co-sputtering from a metallic indium target. After deposition, samples were annealed at 700° C. in an $O_2$ atmosphere. PSS substrates were sourced from Precision Micro-Optics Inc.

Figure 12A:
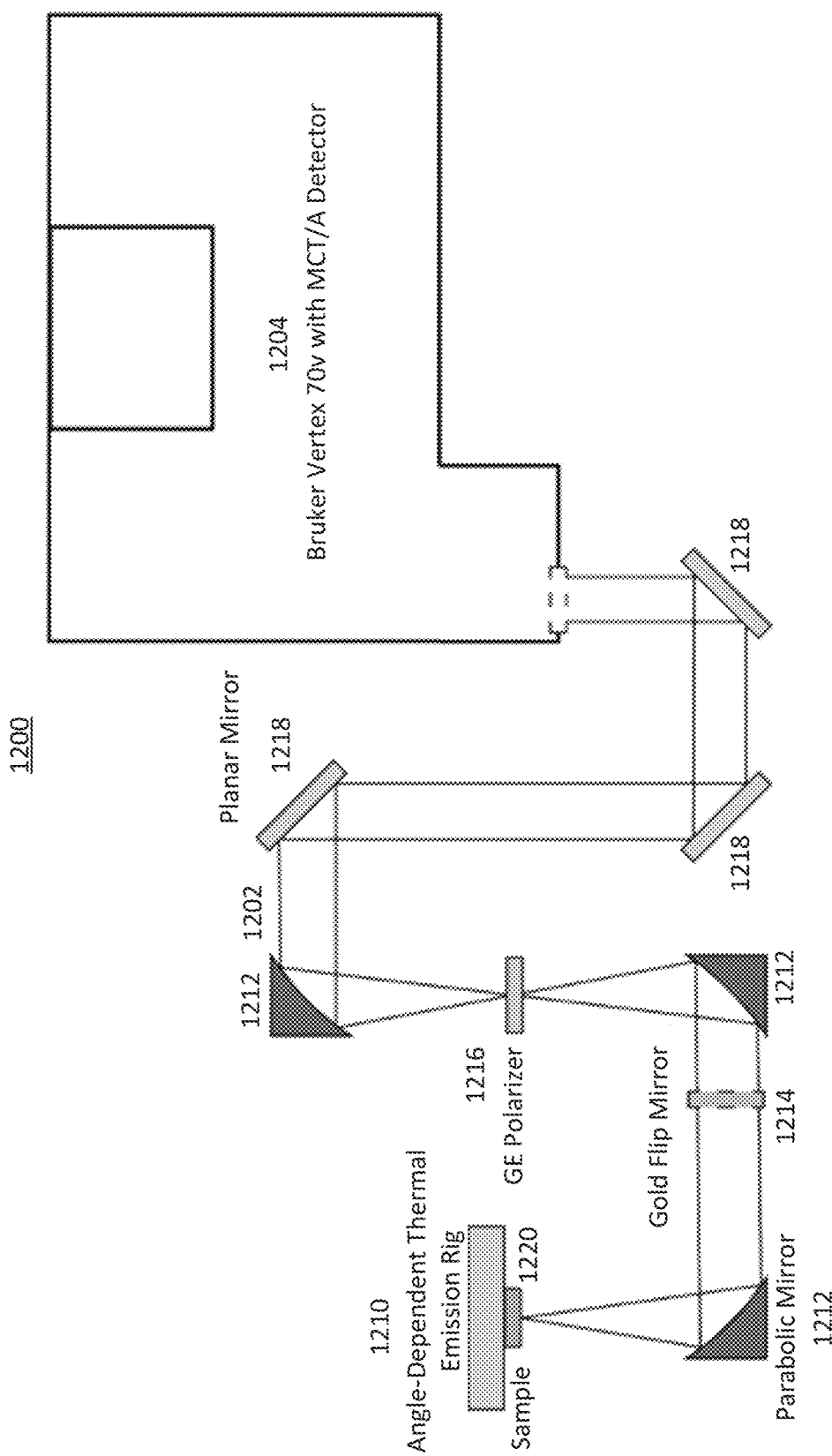

Thermal emission was measured using a Bruker Vertex 70v FTIR along with a custom external thermal emission setup. An image of the thermal emission setup is included in the supplementary information. The sample was mounted on a vertically-oriented hot plate equipped with a Venturi vacuum. Using a combination of micrometers and servo motors, this hot plate grants five degrees of freedom including xyz-position control as well as polar and azimuthal angle control. An aperture was placed in the beam path between the hot plate and a focusing parabolic mirror with the purpose of limiting the detected solid angle to an approximate 0.5 cm diameter spot size, cutting out any emission that could be from the hot plate. A schematic of a system 1200 showing the beam path 1202 for the angle-dependent thermal emission measurements is illustrated in FIG. 12A. The emission from the sample 1220 was then guided and collected through a KBr window and into the FTIR 1204 internal beam path. For polarized thermal emission measurements, a Ge polarizer 1216 was placed in the beam path 1202 between the mirror and pinhole (location noted in FIG. 12A) and measurements were conducted as is described for the unpolarized measurements. In this configuration the emitted signal passes through the interferometer block, taking the place of the spectrometer's internal broadband source which is turned off. The signal was measured using an IR labs mercury-cadmium-telluride (MCT) detector. In order to calculate angle-dependent emissivity, thermal emission measurements were taken at every 10° from 0° to 80° for the CdO devices at 250° C. These measurements were then compared to the thermal emission measured from an emissivity standard at the same temperature and angle of emission. 500 μm tall vertically aligned carbon nanotubes (VACNTs) grown on a Si substrate from an Fe-nanoparticle catalyst, grown by Nanotechlabs Inc., were used as an emissivity standard ($\epsilon$~0.97). These VACNTs provide a high, consistent value for emissivity that is spectrally flat throughout the IR and stable with temperature. The signal collected by the MCT detector in these measurements contains the emission from both the sample as well as the internal optics of the FTIR.

$$M(T_{sample}, T_{ambient}, \lambda, \theta) = R(T_{ambient}, \lambda A)[S(T_{sample}, \lambda, \theta) + G(T_{ambient}, \lambda)] \quad (1)$$

Here, M is the total measured signal, R is a response function for the internal and external optics, S is the signal originating from the sample and G is the 'background' emission from the internal optics. Thus, in order to isolate the signal from the sample, a background measurement was taken by placing a gold mirror in the beam path in front of the hot plate. The resulting spectrum is a product of the response function R with the background emission G. Once the sample, emissivity standard and background emission have been measured we can rearrange equation (1).

$$R(T_{ambient}, \lambda) S_{sample}(T_{sample}, \lambda, \theta) = M_{sample}(T_{sample}, T_{ambient}, \lambda, \theta) - R(T_{ambient}, \lambda) G(T_{ambient}, \lambda) \quad (2)$$

$$R(T_{ambient}, \lambda) S_{standard}(T_{sample}, \lambda, \theta) = M_{standard}(T_{sample}, T_{ambient}, \lambda, \theta) - R(T_{ambient}, \lambda) G(T_{ambient}, \lambda) \quad (3)$$

Assuming no fluctuations in the ambient temperature the response function can be normalized out by taking the ratio of equation (2) to (3) and the emissivity relative to the standard can be determined.

$$\frac{R(T_{ambient}, \lambda) S_{sample}(T_{sample}, \lambda, \theta)}{R(T_{ambient}, \lambda) S_{standard}(T_{sample}, \lambda, \theta)} = \quad (4)$$

$$\frac{S_{sample}(T_{sample}, \lambda, \theta)}{S_{standard}(T_{sample}, \lambda, \theta)} = \varepsilon(T_{sample}, \lambda, \theta)$$

Numerical simulations were performed using CST studio suite 2018. The carrier concentration and electron mobility of the CdO film were measured with Hall effect measurements in the Van der Pauw configuration. With these values, the dielectric function was calculated using the model presented in [25]. A hexagonal unit cell was used for both the CdO on PSS and planar CdO devices and unit cell boundary conditions were used. The geometry of the PSS cone was determined from SEM images taken at Vanderbilt University. The origin of the polar angle lies along the [11$\bar{2}$0] axis of the hexagonal unit cell. Simulated angle-dependent absorption spectra were obtained by taking the ratio of power loss in CdO to input waveguide port power. The Berreman/ENZ mode dispersion provided in S4 of the supplementary information was calculated using the Transfer Matrix Method. [37].

FIG. 12A illustrates a system 1200 for experimentally measuring transmission. The transmission measurements of several concentrations of $CO_2$ were performed using a Bruker Vertex 70v FTIR 1204 along with a Pike short-path gas cell with KRSS windows. Just as with the angle dependent thermal emission measurements, the CdO PSS NIREM or the VACNT blackbody standard was used in lieu of the globar source in the FTIR. The beam path 1202 for these measurements is shown in FIG. 12A. In the example system 1200, the beam path 1202 passes from an angle-dependent thermal emission rig 1210 through parabolic mirrors 1212, a gold flip mirror 1214, a polarizer 1216, planar mirrors 1218 before entering the FTIR 1204. A sample 1220 is shown adjacent to the angle-dependent thermal emission rig 1210.

Figure 12B:
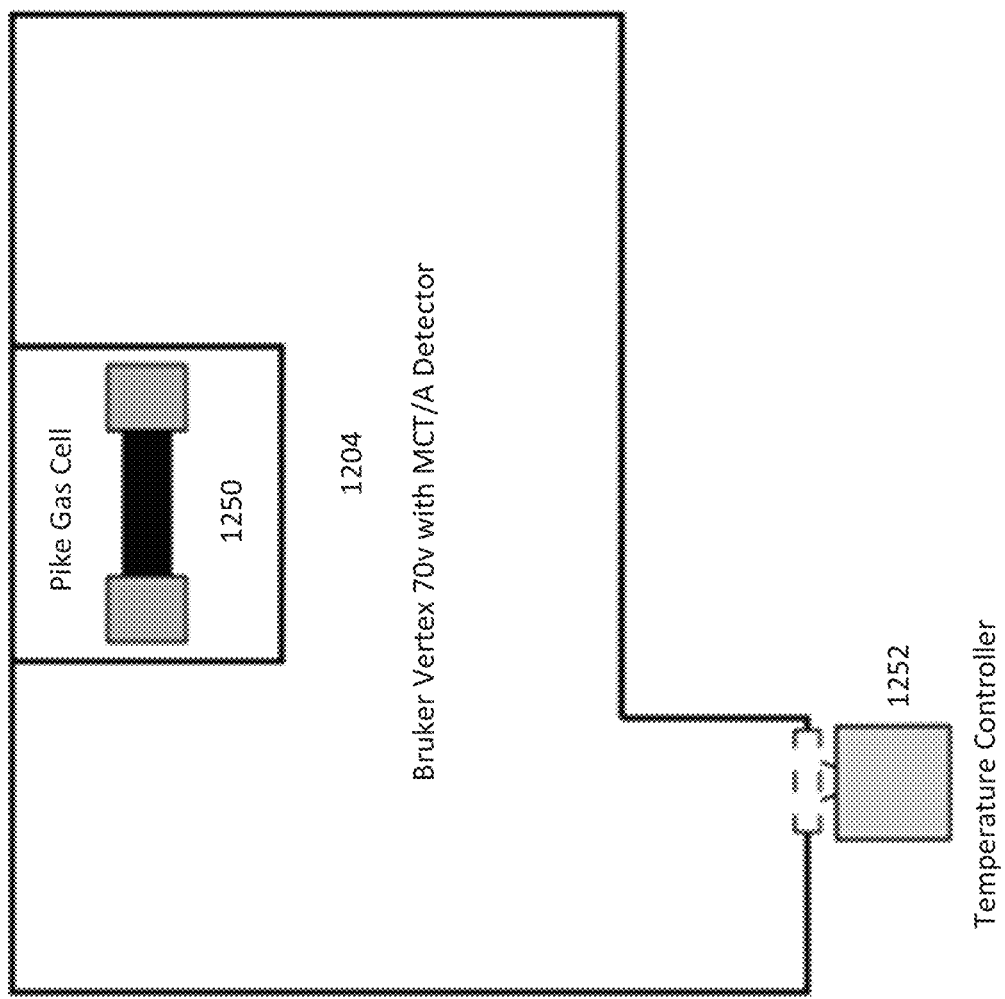

In an experiment, the sample is placed on a temperature controller located at a backport of the FTIR. The sample was heated to 250° C. and the emission was directed into the FTIR 1204 at an angle normal from the sample surface. The gas cell (e.g., the pike gas cell 1250 shown in FIG. 12B) was placed in the sample compartment of the FTIR 1204 which was under a constant $N_2$ purge. FIG. 12B illustrates a view of the FTIR 1204 according to an experiment described herein. An example of a pike gas cell 1250 is illustrated in the FTIR 1204 in FIG. 12B. Optionally, the system 1200 further includes a temperature controller 1252, shown in FIG. 12B. The remainder of the FTIR bench was also under a constant $N_2$ purge. The gas cell is equipped with 4 ports, 2 external ports for $N_2$ purging of the areas outside of the gas cell windows and 2 internal (inlet and outlet) ports for supplying gas to the gas cell. The gas cell was initially purged with $N_2$ until the spectrum from the sample reached a steady state. The gas cell was then sealed (outlet valve shut) and a background transmission measurement was recorded under $N_2$ purge. The outlet valve was then opened and the gas cell was filled with $CO_2/N_2$ mixture calibration gases with varying $CO_2$ concentrations from GASCO. As with the background spectrum, the $CO_2/N_2$ calibration gas was allowed to flow until the spectrum reached a steady state, after which the outlet valve was closed and measurements were collected.

The various embodiments described above are provided by way of illustration only and should not be construed to limit the scope of the present disclosure. The patentable scope of certain embodiments of the present disclosure is indicated by the claims here appended, rather than the foregoing description, and all changes that come within the meaning and range of equivalents thereof are intended to be embraced therein.

LIST OF REFERENCES

[1] G. ed. Sberveglieri, *Gas Sensors: Principles, Operation and Developments*. (Kluwer, Boston, 1992).
[2] J. R. Meyer, I. Vurgaftman, C. L. Canedy, W. W. Bewley, C. S. Kim, C. D. Merritt, M. V. Warren, and M. Kim, (2019).
[3] A. Lochbaum, A. Dorodnyy, U. Koch, S. M. Koepfli, S. Volk, Y. Fedoryshyn, V. Wood, and J. Leuthold, Nano Lett. 20, 4169 (2020).
[4] J. Hodgkinson and R. P. Tatam, 24, 43 (2013).
[5] F. H. L. Koppens, T. Mueller, P. Avouris, A. C. Ferrari, M. S. Vitiello, and M. Polini, Nat. Nanotechnol. 9, 780 (2014).
[6] T. G. Folland, L. Nordin, D. Wasserman, and J. D. Caldwell, J. Appl. Phys. 125, (2019).
[7] M. De Zoysa, T. Asano, K. Mochizuki, A. Oskooi, T. Inoue, and S. Noda, Nat. Photonics 6, 535 (2012).
[8] M. Laroche, R. Carminati, and J. Greffet, (2014).
[9] T. Inoue, M. De Zoysa, T. Asano, and S. Noda, 24, 899 (2016).
[10] J. J. Greffet, R. Carminati, K. Joulain, J. P. Mulet, S. Mainguy, and Y. Chen, Nature 416, 61 (2002).
[11] G. Lu, R. J. Nolen, T. G. Folland, M. Tadjer, D. G. Walker, and J. D. Caldwell, ACS Omega (n.d.).
[12] T. Wang, P. Li, D. N. Chigrin, A. J. Giles, F. J. Bezares, O. J. Glembocki, J. D. Caldwell, and T. Taubner, ACS Photonics 4, 1753 (2017).
[13] J. A. Schuller, T. Taubner, and M. L. Brongersma, Nat. Photonics 3, 658 (2009).
[14] A. Howes, J. R. Nolen, J. D. Caldwell, and J. Valentine, Adv. Opt. Mater. 8, 1 (2020).
[15] J. A. Mason, S. Smith, and D. Wasserman, 241105, 15 (2011).
[16] D. G. Baranov, Y. Xiao, I. A. Nechepurenko, A. Krasnok, A. Alù, and M. A. Kats, Nat. Mater. 18, 920 (2019).
[17] J. D. Caldwell, O. J. Glembocki, Y. Francescato, N. Sharac, V. Giannini, F. J. Bezares, J. P. Long, J. C. Owrutsky, I. Vurgaftman, J. G. Tischler, V. D. Wheeler, N. D. Bassim, L. M. Shirey, R. Kasica, and S. A. Maier, Nano Lett. 13, 3690 (2013).
[18] X. Liu, T. Tyler, T. Starr, A. F. Starr, N. M. Jokerst, and W. J. Padilla, Phys. Rev. Lett. 107, 4 (2011).
[19] N. I. Landy, S. Sajuyigbe, J. J. Mock, D. R. Smith, and W. J. Padilla, (2008).
[20] A. Lochbaum, Y. Fedoryshyn, A. Dorodnyy, U. Koch, C. Hafner, and J. Leuthold, ACS Photonics 4, 1371 (2017).
[21] S. Vassant, J.-P. Hugonin, F. Marquier, and J.-J. Greffet, Opt. Express 20, 23971 (2012).
[22] S. Campione, I. Brener, and F. Marquier, Phys. Rev. B 91, 121408 (2015).
[23] K. P. Kelley, E. Sachet, C. T. Shelton, and J. P. Maria, APL Mater. 5, 0 (2017).
[24] E. L. Runnerstrom, K. P. Kelley, E. Sachet, C. T. Shelton, and J. P. Maria, ACS Photonics (2017).
[25] J. R. Nolen, E. L. Runnerstrom, K. P. Kelley, T. S. Luk, T. G. Folland, A. Cleri, J.-P. Maria, and J. D. Caldwell, Phys. Rev. Mater. 4, 1 (2020).
[26] K. P. Kelley, E. L. Runnerstrom, E. Sachet, C. T. Shelton, E. D. Grimley, A. Klump, J. M. Lebeau, Z. Sitar, J. Y. Suen, W. J. Padilla, and J.-P. Maria, ACS Photonics 6, 1139 (2019).
[27] E. Sachet, C. T. Shelton, J. S. Harris, B. E. Gaddy, D. L. Irving, S. Curtarolo, B. F. Donovan, P. E. Hopkins, P. A. Sharma, A. L. Sharma, J. Ihlefeld, S. Franzen, and J. P. Maria, Nat. Mater. 14, 414 (2015).
[28] M. Malerba, A. Alabastri, E. Miele, P Zilio, M. Patrini, D. Bajoni, G. C. Messina, M. Dipalo, A. Toma, R. P. Zaccaria, and F. De Angelis, Nat. Sci. Reports 5, (2015).
[29] A. G. Nikitin, A. V Kabashin, and H. Dallaporta, 20, 27941 (2012).
[30] V. G. Kravets, F. Schedin, and A. N. Grigorenko, 087403, 1 (2008).
[31] V. Giannini, Y. Francescato, H. Amrania, C. C. Phillips, and S. A. Maier, Nano Lett. 11, 2835 (2011).
[32] B. S. Simpkins, J. P. Long, O. J. Glembocki, J. Guo, and J. D. Caldwell, 20, 18178 (2012).
[33] R. Adato, A. A. Yanik, J. J. Amsden, D. L. Kaplan, F. G. Omenetto, M. K. Hong, S. Erramilli, and H. Altug, Proc. Natl. Acad. Sci. 106, 19227 (2009).
[34] R. Adato, A. Artar, S. Erramilli, and H. Altug, (2013).
[35] P. J. Linstrom, W. G. Mallard, and (eds.), *NIST Chemistry WebBook, NIST Standard Reference Database Number 69* (National Institute of Standards and Technology, Gaithersburg MD, n.d.).
[36] E. L. Runnerstrom, K. P. Kelley, E. Sachet, C. T. Shelton, and J. P. Maria, ACS Photonics 4, 1885 (2017).
[37] N. C. Passler and A. Paarmann, J. Opt. Soc. Am. B 34, 2128 (2017).
[38] P. J. Linstrom, W. G. Mallard, and (eds.), NIST Chemistry WebBook, NIST Standard Reference Database Number 69 (National Institute of Standards and Technology, Gaithersburg MD, n.d.).

What is claimed is:

1. A non-dispersive infrared (NDIR) sensor, comprising:
a nanophotonic infrared emitting metamaterial (NIREM) emitter configured to selectively emit radiation corresponding to a respective vibrational resonance frequency for each of a plurality of different analytes of interest; and
a broadband detector configured to detect photons from the NIREM emitter, including photons associated with interactions of the emitted radiation from the NIREM emitter with an analyte of interest and corresponding to the respective vibrational resonance frequency, such as to determine one or more properties of the analyte of interest.

2. The sensor of claim 1, wherein the one or more properties comprise the concentration of at least one of the analytes of interest.

3. The sensor of claim 1, wherein the NIREM emitter comprises a plurality of different emitters, each configured to emit radiation corresponding to a vibrational resonance frequency of a different analyte of interest.

4. The sensor of claim 3, wherein each of the plurality of different emitters is selectively and individually activatable for emission.

5. The sensor of claim 4, wherein the NIREM emitter is configured such that:
   a first emitter of the plurality of different emitters is activatable at a first time to emit radiation corresponding to a vibrational resonance frequency of a first analyte of interest; and
   a second emitter of the plurality of different emitters is activatable at a second time to emit radiation corresponding to a vibrational resonance frequency of a second analyte of interest,
   wherein the first time is different from the second time and the first analyte of interest is different from the second analyte of interest.

6. The sensor of claim 3, wherein the plurality of different emitters are arranged in an array.

7. The sensor of claim 1, wherein the NIREM emitter comprises a patterned sapphire substrate (PSS) combined with a CdO film supporting an ENZ/Berreman optical mode.

8. The sensor of claim 1, wherein the NIREM emitter is configured for s-polarized thermal emission and/or p-polarized thermal emission.

9. The sensor of any one of claim 1, wherein the broadband detector comprises a thermopile.

10. The sensor of claim 1, wherein the plurality of different analytes of interest comprises $CO_2$.

11. A method for non-dispersive infrared (NDIR) sensing, comprising:
    selectively emitting, by a nanophotonic infrared emitting metamaterial (NIREM) emitter, radiation corresponding to a respective vibrational resonance frequency of each of a plurality of different analytes of interest; and
    detecting, by a broadband detector, photons associated with vibrational activity of the analytes of interest in response to the emitted radiation.

12. The method of claim 11, further comprising:
    determining, based on the photon detection, one or more properties of at least one of the analytes of interest.

13. The method of claim 12, wherein the one or more properties comprise the concentration of at least one of the analytes of interest.

14. The method of claim 11, wherein the NIREM emitter comprises a plurality of different emitters, each configured to emit radiation corresponding to a vibrational resonance frequency of one or more analytes of interest.

15. The method of claim 14, wherein each of the plurality of different emitters is selectively and individually activatable for emission, and wherein the step of selectively emitting radiation comprises:
    selectively activating a first emitter of the plurality of different emitters, at a first time, to emit radiation corresponding to a vibrational resonance frequency of a first analyte of interest, and selectively activating a second emitter of the plurality of different emitters, at a second time, to emit radiation corresponding to a vibrational resonance frequency of a second analyte of interest, wherein the first time is different from the second time and the first analyte of interest is different from the second analyte of interest.

16. The method of claim 14, wherein the plurality of different emitters are arranged in an array.

17. The method of claim 11, wherein the NIREM emitter comprises a patterned sapphire substrate (PSS) combined with a CdO film supporting an ENZ/Berreman optical mode.

18. The method of claim 11, wherein the NIREM emitter is configured for s-polarized thermal emission and/or p-polarized thermal emission.

19. The method of claim 11, wherein the broadband detector comprises a thermopile.

20. The method of claim 11, wherein the plurality of different analytes of interest comprises $CO_2$.

* * * * *